(12) United States Patent
Friedl et al.

(10) Patent No.: US 8,715,728 B2
(45) Date of Patent: May 6, 2014

(54) EXTENDED RELEASE PELLET FORMULATION CONTAINING PRAMIPEXOLE OR A PHARMACEUTICALLY ACCEPTABLE SALT THEREOF

(75) Inventors: Thomas Friedl, Ochsenhausen (DE); Rolf-Stefan Brickl, Warthausen (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 323 days.

(21) Appl. No.: 12/630,271

(22) Filed: Dec. 3, 2009

(65) Prior Publication Data

US 2010/0086589 A1    Apr. 8, 2010

Related U.S. Application Data

(63) Continuation of application No. 12/276,610, filed on Nov. 24, 2008, now abandoned, which is a continuation of application No. 11/202,689, filed on Aug. 12, 2005, now abandoned.

(30) Foreign Application Priority Data

Aug. 13, 2004 (EP) .................... 04019249

(51) Int. Cl.
| | | |
|---|---|---|
| A61K 9/22 | (2006.01) |
| A61K 9/62 | (2006.01) |
| A61K 9/58 | (2006.01) |
| A61K 9/16 | (2006.01) |
| A61K 9/50 | (2006.01) |
| A61K 31/425 | (2006.01) |

(52) U.S. Cl.
USPC ........... 424/468; 424/461; 424/462; 424/490; 424/494; 424/497; 514/367; 427/2.21

(58) Field of Classification Search
USPC ................. 424/468, 461, 462, 490, 494, 497; 514/367; 427/2.21
See application file for complete search history.

(56) References Cited

U.S. PATENT DOCUMENTS

| | | | |
|---|---|---|---|
| 2,887,440 | A | 5/1959 | Greminger, Jr. et al. |
| 3,065,143 | A | 11/1962 | Christenson et al. |
| 3,074,852 | A | 1/1963 | Mayron |
| 3,458,622 | A | 7/1969 | Hill |
| 3,845,770 | A | 11/1974 | Theeuwes et al. |
| 4,036,948 | A | 7/1977 | Kitamori et al. |

(Continued)

FOREIGN PATENT DOCUMENTS

| | | |
|---|---|---|
| CA | 1263653 | 12/1989 |
| CA | 2455585 | 2/2003 |

(Continued)

OTHER PUBLICATIONS

The Merck Index; Thirteenth Edition; Merck & Co., Inc., Whitehouse Station, NJ, USA, 2001, pp. 7790-7791.

(Continued)

*Primary Examiner* — Aradhana Sasan
(74) *Attorney, Agent, or Firm* — Michael P. Morris; Philip I. Datlow

(57) ABSTRACT

An extended release pellet comprising an active ingredient selected from pramipexole and the pharmaceutically acceptable salts thereof, and at least one release-modifying excipient.

16 Claims, 5 Drawing Sheets

(56) References Cited

U.S. PATENT DOCUMENTS

| | | | |
|---|---|---|---|
| 4,140,755 A | 2/1979 | Sheth et al. | |
| 4,167,558 A | 9/1979 | Sheth et al. | |
| 4,389,393 A | 6/1983 | Schor et al. | |
| 4,424,235 A | 1/1984 | Sheth et al. | |
| 4,656,027 A | 4/1987 | Sjoovist | |
| 4,666,612 A | 5/1987 | Hoffman et al. | |
| 4,709,712 A | 12/1987 | Bordovsky et al. | |
| 4,731,374 A | 3/1988 | Griss et al. | |
| 4,738,851 A | 4/1988 | Schoenwald et al. | |
| 4,789,549 A | 12/1988 | Khan et al. | |
| 4,886,812 A | 12/1989 | Griss et al. | |
| 4,968,508 A | 11/1990 | Oren et al. | |
| 5,007,790 A | 4/1991 | Shell | |
| 5,026,559 A | 6/1991 | Eichel et al. | |
| 5,078,991 A | 1/1992 | Birtwistle et al. | |
| 5,133,974 A | 7/1992 | Paradissis et al. | |
| 5,273,975 A | 12/1993 | Moon et al. | |
| 5,370,879 A | 12/1994 | Masterson et al. | |
| 5,431,920 A | 7/1995 | Bechard | |
| 5,458,887 A | 10/1995 | Chen et al. | |
| 5,472,712 A | 12/1995 | Oshlack et al. | |
| 5,656,296 A | 8/1997 | Khan et al. | |
| 5,731,338 A | 3/1998 | Acharya | |
| 5,846,971 A * | 12/1998 | Sangekar et al. | 514/254.07 |
| 6,056,977 A | 5/2000 | Bhagwat et al. | |
| 6,126,959 A | 10/2000 | Levine et al. | |
| 6,191,153 B1 | 2/2001 | Hammer et al. | |
| 6,197,339 B1 | 3/2001 | Ju | |
| 6,221,396 B1 | 4/2001 | Chao et al. | |
| 6,248,358 B1 | 6/2001 | Bologna et al. | |
| 6,277,875 B1 | 8/2001 | Holman | |
| 6,316,031 B1 * | 11/2001 | Oshlack et al. | 424/495 |
| 6,340,475 B2 | 1/2002 | Shell et al. | |
| 6,417,177 B1 | 7/2002 | Nelson | |
| 6,451,343 B1 | 9/2002 | Glinecke et al. | |
| 6,467,637 B2 | 10/2002 | Riga | |
| 6,558,701 B2 | 5/2003 | Bartholomaeus et al. | |
| 6,624,200 B2 | 9/2003 | Bologna et al. | |
| 6,667,060 B1 | 12/2003 | Vandecruys et al. | |
| 6,689,384 B2 | 2/2004 | Tenengauzer et al. | |
| 6,727,367 B2 | 4/2004 | Pospisilik | |
| 7,153,845 B2 | 12/2006 | Levine et al. | |
| 7,695,734 B2 | 4/2010 | Friedl et al. | |
| 8,545,886 B2 | 10/2013 | Eisenreich et al. | |
| 2001/0041727 A1 | 11/2001 | Marshall et al. | |
| 2001/0042727 A1 | 11/2001 | Riga | |
| 2002/0010216 A1 | 1/2002 | Rogosky et al. | |
| 2002/0015735 A1 | 2/2002 | Hedden et al. | |
| 2002/0103240 A1 | 8/2002 | Pospisilik | |
| 2002/0114831 A1 | 8/2002 | Norden et al. | |
| 2002/0132850 A1 | 9/2002 | Bartholomaeus et al. | |
| 2002/0182256 A1 | 12/2002 | Oh et al. | |
| 2003/0032661 A1 | 2/2003 | Croenlein | |
| 2003/0049318 A1 | 3/2003 | Davis et al. | |
| 2003/0077297 A1 | 4/2003 | Chen et al. | |
| 2003/0133982 A1 | 7/2003 | Heimlich et al. | |
| 2003/0180352 A1 | 9/2003 | Patel et al. | |
| 2003/0215498 A1 | 11/2003 | Harland | |
| 2004/0001887 A1 | 1/2004 | Levine et al. | |
| 2004/0068119 A1 | 4/2004 | Pospisilik | |
| 2004/0122104 A1 | 6/2004 | Hirsh et al. | |
| 2005/0020589 A1 | 1/2005 | Ganorkar et al. | |
| 2005/0175691 A1 | 8/2005 | Lee et al. | |
| 2005/0226926 A1 | 10/2005 | Amidon et al. | |
| 2006/0051417 A1 | 3/2006 | Friedl et al. | |
| 2006/0051419 A1 | 3/2006 | Friedl et al. | |
| 2006/0198887 A1 | 9/2006 | Friedl et al. | |
| 2007/0196481 A1 | 8/2007 | Amidon et al. | |
| 2008/0031945 A1 | 2/2008 | Eisenreich et al. | |
| 2008/0038346 A1 | 2/2008 | Eisenreich et al. | |
| 2008/0069873 A1 | 3/2008 | Pearnchob et al. | |
| 2009/0041844 A1 | 2/2009 | Friedl et al. | |
| 2009/0098202 A1 | 4/2009 | Friedl et al. | |
| 2009/0130197 A1 | 5/2009 | Friedl et al. | |
| 2009/0143387 A1 | 6/2009 | Amidon et al. | |
| 2009/0182024 A1 | 7/2009 | Friedl et al. | |
| 2009/0281153 A1 | 11/2009 | Friedl et al. | |
| 2010/0086589 A1 | 4/2010 | Friedl et al. | |

FOREIGN PATENT DOCUMENTS

| | | | |
|---|---|---|---|
| EP | 0 040 590 A2 * | 11/1981 | ............... A61K 9/22 |
| EP | 0425154 A1 | 5/1991 | |
| EP | 0661045 A1 | 7/1995 | |
| EP | 0895780 | 2/1999 | |
| EP | 0933079 | 8/1999 | |
| ES | 2164940 T3 | 3/2002 | |
| GB | 2097676 | 11/1982 | |
| GB | 2338186 | 12/1999 | |
| JP | 63258420 A | 10/1988 | |
| JP | 4234812 A | 8/1992 | |
| JP | 2003510268 A | 3/2003 | |
| JP | 2003512311 A | 4/2003 | |
| JP | 2003522144 A | 7/2003 | |
| JP | 2004043478 A | 2/2004 | |
| MX | 174157 B | 4/1994 | |
| WO | 9015058 A1 | 12/1990 | |
| WO | 9201443 A1 | 2/1992 | |
| WO | 9618395 A1 | 6/1996 | |
| WO | 9704752 | 2/1997 | |
| WO | 9810762 A2 | 3/1998 | |
| WO | 9855107 | 12/1998 | |
| WO | 9901111 A1 | 1/1999 | |
| WO | 9901121 | 1/1999 | |
| WO | 9909066 | 2/1999 | |
| WO | 9916422 A1 | 4/1999 | |
| WO | 9945924 | 9/1999 | |
| WO | 9959563 A2 | 11/1999 | |
| WO | 0001369 A1 | 1/2000 | |
| WO | 0010536 | 3/2000 | |
| WO | 0023055 A1 | 4/2000 | |
| WO | 0027370 A1 | 5/2000 | |
| WO | 0059477 | 10/2000 | |
| WO | 0101973 | 1/2001 | |
| WO | 0110405 | 2/2001 | |
| WO | 0119337 | 3/2001 | |
| WO | 0122820 | 4/2001 | |
| WO | 0122944 A1 | 4/2001 | |
| WO | 0205797 A2 | 1/2002 | |
| WO | 0222591 A1 | 3/2002 | |
| WO | 03011300 A1 | 2/2003 | |
| WO | 03011301 A1 | 2/2003 | |
| WO | 03013521 | 2/2003 | |
| WO | 2003011255 A1 | 2/2003 | |
| WO | 2003035042 A1 | 5/2003 | |
| WO | WO 03/053402 | 7/2003 | |
| WO | 03075887 A1 | 9/2003 | |
| WO | 03084504 A2 | 10/2003 | |
| WO | 2004002398 A2 | 1/2004 | |
| WO | 2004010997 | 2/2004 | |
| WO | 2004010998 | 2/2004 | |
| WO | WO 2004/010982 A1 | 2/2004 | |
| WO | WO 2004/010999 A1 | 2/2004 | |
| WO | 2004058228 A1 | 7/2004 | |
| WO | 2004058229 A1 | 7/2004 | |
| WO | 2004080440 | 9/2004 | |
| WO | WO 2004/087175 A1 | 10/2004 | |
| WO | 2006015942 | 2/2006 | |
| WO | 2006015943 | 2/2006 | |
| WO | 2006015944 | 2/2006 | |
| WO | 2006046256 | 5/2006 | |
| WO | 2007002516 | 1/2007 | |
| WO | 2007002518 | 1/2007 | |
| WO | 2007022182 | 2/2007 | |
| WO | 2007054976 | 5/2007 | |
| WO | 2007090881 | 8/2007 | |
| WO | 2007090882 | 8/2007 | |
| WO | 2007090883 | 8/2007 | |
| WO | 2008015162 | 2/2008 | |

OTHER PUBLICATIONS

Remington Farmacia 1988; Alfonso R. Gennaro; 19a Edition; Panamericana Espana; pp. 2470.

(56) References Cited

OTHER PUBLICATIONS

Hubble; Pre-clinical studies of pramipexole: clinical relevance; European Journal of Neurology Suppl.; May 2000; vol. 7; No. Supplement 1; pp. 15-20.
Nur et al.; Captopril Floating and/or Bioadhesive Tablets: Design and Release Kinetics; Drug Development and Industrial Pharmacy; 2000; vol. 26; No. 9; pp. 965-969.
Santus; An in vitro-in viro investigation of oral bioadhesive controlled release furosemide formulations; European Journal of Pharmaceutics and Biopharmaceutics; 1997; vol. 44; pp. 39-52.
Elkheshen et al.; In vitro and in vivo Evaluation of Floating Controlled Release Dosage Forms of Verapamil Hydrochloride; Pharm. Ind.; 2004; vol. 66; No. 11; pp. 1364-1372.
Elkheshen et al.; Per-oral Extended-Release Bioadhesive Tablet Formulation of Verapamil HC1; Bollettino Chimico Farmaceutico, Societa Editoriale Farmaceutica, Milano, 2002; vol. 142; No. 5; pp. 226-231.
Biglan et al.; A review of pramipexole and its clinical utility in Parkinson's disease; Expert Opinion on Pharmacotherapy; 2002; vol. 3; No. 2; pp. 197-210.
Colosimo et al.; Motor fluctuations in Parkinson's disease: pathophysiology and treatment; European Journal of Neurology; 1999; vol. 6; No. 1; pp. 1-21.
Dooley et al.; Pramipexole: A Review of its Use in the Management of Early and Advanced Parkinson's Disease; Drugs & Aging; 1998; vol. 12; No. 6; pp. 495-514.
Hiestand et al.; Indices of Tableting Performance; Powder Technology; 1984; vol. 38; pp. 145-159.
Hiestand et al.; Tablet bond. II. Experimental check of model; International Journal of Pharmaceutics; 1991; vol. 67; pp. 231-246.
Hubble et al.; Pramipexole in Patients with Early Parkinson's Disease; Clinical Neuropharmacology; vol. 18; No. 4; pp. 338-347, 1995.
Wright et al.; Steady-State Pharmacokinetic Properties of Pramipexole in Healthy Volunteers; Journal of Clinical Pharmacology; 1997; vol. 37; pp. 520-525.
USP 24th Edition; 2000; pp. 1941-1943.
Physicians' Desk Reference; 37th Edition; 2003; pp. 2768-2772.
British National Formulary; 41st ed.; 2001; 196.
Lemke; Effect of Reboxetine on Depression in Parkinson's Disease in Patients; Journal of Clinical Psychiatry; 2002; vol. 63; No. 4; pp. 300-304.
Mierau et al.; Pramipexole binding and activation of cloned and expressed dopamine D2, D3 and D4 receptors; European Journal of Pharmacology Molecular Pharmacology Section 290; 1995; pp. 29-36.
Mierau; Pramipexole: A Dopamine-Receptor Agonist for Treatment of Parkinson's Disease; Clinical Neuropharmacology; vol. 18; Supp 1; 1995 Raven Press; pp. S195-S206.
Tonson et al.; Compaction Properties of Pregelantized Starch (Starch 1500 TM): Self-Lubrication; abstract taken from AIChE 2006 Spring National Meeting Preliminary Program.
Non-final Office Action dated Oct. 13, 2006 from U.S. Appl. No. 10/626,275, filed Jul. 24, 2003; Lee et al.
Response to Restriction Requirement dated Mar. 12, 2007 from U.S. Appl. No. 10/626,275, filed Jul. 24, 2003; Lee et al.
Non-final Office Action dated Jun. 11, 2007 from U.S. Appl. No. 10/626,275, filed Jul. 24, 2003; Lee et al.
Amendment dated Dec. 7, 2007 from U.S. Appl. No. 10/626,275, filed Jul. 24, 2003; Lee et al.
Non-final Office Action dated May 29, 2008 from U.S. Appl. No. 10/626,275, filed Jul. 24, 2003; Lee et al.
Amendment and Terminal Disclaimer dated Nov. 26, 2008 from U.S. Appl. No. 10/626,275, filed Jul. 24, 2003; Lee et al.
Interview Summary Form dated Dec. 3, 2008 from U.S. Appl. No. 10/626,275, filed Jul. 24, 2003; Lee et al.
Final Office Action dated Feb. 19, 2009 from U.S. Appl. No. 10/626,275, filed Jul. 24, 2003; Lee et al.
Non-final Office Action dated Sep. 4, 2009 from U.S. Appl. No. 10/626,166, filed Jul. 23, 2003; Amidon et al.
Oct. 5, 2009 Response to Request for Information from U.S. Appl. No. 10/626,166, filed Jul. 24, 2003; Lee et al.
Non-final Office Action dated Nov. 12, 2009 from U.S. Appl. No. 10/626,275, filed Jul. 24, 2003; Lee et al.
Scheife et al.; Impact of Parkinson's disease and its pharmacologic treatment on quality of life and economic outcomes; U.S. National Library of Medicine; 2000; XP002314706.
Perez-Marcos et al.; Release of propranolol hydrochloride from matrix tablets containing hydroxypropylmethylcellulose K4M and carbopol 974; International Journal of Pharmaceutics; 1994; vol. 111; pp. 251-259.
Franz et al.; In Vitro Evaluation of a Mixed Polymeric Sustained Release Matrix Using Response Surface Methodology; Journal of Controlled Release; 1987; vol. 5; pp. 159-172.
Abdallah et al.; Preparation and evaluation of metformin hydrochloride controlled-release tablets; STP Pharma; 1988; vol. 4; pp. 15-20.
Huang et al.; Studies on Drug Release from a Carbomer Tablet Matrix; Drug Development and Industrial Pharmacy; 1995; vol. 21; No. 13; pp. 1487-1501.
Gupta et al.; Hydrogels: from controlled release to pH-responsive drug delivery; Drug Discovery Today; May 2002; vol. 7; No. 10; pp. 569-579.
Li et al.; Effect of HPMC and Carbopol on the release and floating properties of Gastric Floating Drug Delivery System using factorial design; International Journal of Pharmaceutics; 2003; vol. 253; pp. 13-22.
Perez-Marcos et al.; Influence of pH on the Release of Propranolol Hydrochloride from Matrices Containing Hydroxypropylmethylcellulose K4M and Carbopol 974; Journal of Pharmaceutical Sciences; Mar. 1996; vol. 85; No. 3; pp. 330-334.
Huber et al.; Utilization of Jydrophilic Gums for the Control of Drug Substance Release from Tablet Formulations II. Influence of Tablet Hardness and Density on DissolutionBehavior; Journal of Pharmaceutical Sciences; 1968; vol. 57; pp. 164-166.
Bonferoni et al.; Rheological behaviour of hydrophilic polymers and drug release from erodible matrices; Journal of Controlled Release 1992; vol. 18; pp. 205-212.
Office Action dated Sep. 4, 2009, U.S. Appl. No. 10/626,166, filed Jul. 23, 2003.
Oct. 5, 2009 Response to Requst for Information, U.S. Appl. No. 10/626,166, filed Jul. 23, 2003.
U.S. Office Action dated Aug. 5, 2009, U.S. Appl. No. 11/202,713.
Abstract in English for Japan JPA7330606, 1995.
Abstract in English for Japan JPA320215, 1991.
Mani et al., Solubility of Guaifenesin in the Presence of Common Pharmaceutical Additives, Pharmaceutical Development and Technology, pp. 385-396, 2003, vol. 8, No. 4.
Bodmeier et al., The influence of buffer species and strength on diltiazem HCl release from beads coated with aqueous cationic polymer dispersions, eudragit RS, RL 30D, Pharmaceutical Research, 1996, vol. 13, No. 1, pp. 52-56.
Young et al., Properties of drug-containing spherical pellets produced by a hot-melt extrusion and spheronization process, Journal of Microencapsulation, 2003, vol. 20, No. 5, pp. 613-625.
British National Formulary, British Medical Association and the Royal Pharmaceutical Society of Great Britain, 2001, p. 242.
Aulton, Pharmaceutics: The Science of dosage form design; First Edition, 1988, Chapter 18.
Bogentoft et al.,Controlled release From Dosage Forms, Towards Better Safety of Drugs and Pharmaceutical Products, 1980, pp. 229-246.
Note for Guidance on Modified Release Oral and Transdermal Dosage Forms: Section II (Pharmacokinetic and Clinical Evaluation), CPMP, 1999, pp. 1-12.
Analysis of SIFROL, Actavis, PRM Dissolution Corrected for Sample Withdrawn At Each Time Point, 2013.
Shannnon et al., Efficacy of pramipexole, a novel dopamine agonist, as monotherapy in mild to moderate Parkinson's disease, Neurology, 1997, vol. 49, No. 3, p. 724-8.
Ansel et al., Introduction to Pharmaceutical Dosage Forms, $th edition, 1985, pp. 167-170.

(56) References Cited

OTHER PUBLICATIONS

Bravo et al., Swellable Matrices for the Controlled-release of Diclofenac Sodium: Formulation and In Vitro Studies, Pharmaceutical Development and Technology, vol. 9, No. 1, 2004, pp. 75-83.

Bulletin 2 Product and Regulatory Guide Pharmaceutical Polymers, Noveon, Jan. 2002, pp. 1-3.

Carbomer, 1st Edition, Handbook of Pharmaceutical Excipients, 1986, pp. 41-42.

Dong et al., effects of physico-chemical properties of hydroxypropylmethylcellulose on dissolution from hydrophilic matrix tablets, Department of Pharmaceutics, Second Military Medical University, vol. 29, No. 12, 1994, pp. 920-924.

Lieberman et al., Pharmaceutical Doasge Forms: Tablets, vol. 1, 1980, pp. 109-116.

Lu et a;., Studies on sustained release hydrophilic matrix tablets containing hydroxypropylmethycellulose and carbopol, Department of Pharmaceutics, School of Pharmacy, Fudan University, vol. 36, No. 9, 2001, pp. 603-606.

Samani et al., The effect of polymer blends on release profiles of diclfenac sodium from matrices, European Journal of Pharmaceutics and Biopharmaceutics, vol. 55, 2003, pp. 351-355.

Su et al., Adsorption properties of heavy metal ions from wastewater with chitosan-chelated bead, Journal of Bejing University of Chemical Technology, vol. 30, No. 2, 2003,pp. 19-22.

Wade et al., Handbook of Pharmaceutical Excipients, Carbomer, 1994, pp. 71-73.

* cited by examiner ns Disease or advanced Parkinson's Disease in combination with levodopa. The IR tablets have to be taken 3 times a day.

From the pharmacokinetic point of view, pramipexole IR tablets are rapidly and completely absorbed following oral administration. The absolute bioavailability is greater than 90% and the maximum plasma concentration occurs within 1 to 3 hours. The rate of absorption is reduced by food intake but not the overall extent of absorption. Pramipexole shows linear kinetics and a relatively small inter-patient variation of plasma levels. The elimination half-life ($t_{1/2}$[h]) varies from 8 hours in the young to 12 hours in the elderly.

As is commonly known, modified release of active ingredient(s) allows simplification of the patient's administration scheme by reducing the amount of recommended daily intakes, improves patient's compliance, and attenuates adverse events, e.g., related to high plasma peaks. Modified release pharmaceutical preparations regulate the release of the incorporated active ingredient or ingredients over time and comprise formulations with a controlled, a prolonged, a sustained, a delayed, a slow or an extended release, so they accomplish therapeutic or convenience objectives not offered by conventional dosage forms such as solutions or promptly dissolving dosage forms.

A modified or extended release of active ingredient(s) from a pharmaceutical preparation may be accomplished by homogeneously embedding the active ingredient(s) in a hydrophilic matrix, being a soluble, partially soluble or insoluble network of viscous, hydrophilic polymers, held together by physical or chemical entanglements, by ionic or crystalline interactions, by complex formation, by hydrogen bonds or van der Waals forces. The hydrophilic matrix swells upon contact with water, thereby creating a protective gel layer from which the active ingredient(s) are slowly, gradually, continuously released in time either by diffusion through the polymeric network, by erosion of the gel layer, by dissolution of the polymer, or by a combination of these release mechanisms.

However, it has proved difficult to formulate a dosage form having a suitable combination of modified, extended, or sustained-release and handling properties, where the drug is one having relatively high solubility, as in the case of pramipexole dihydrochloride.

There are a number of approaches described in prior art to provide controlled release pharmaceutical compositions of pramipexole.

WO 2004/010997 describes a sustained-release pharmaceutical composition in a form of an orally deliverable tablet comprising a water-soluble salt of pramipexole, dispersed in a matrix comprising a hydrophilic polymer and a starch having a tensile strength of at least about 0.15 kN cm$^{-2}$, preferably at least about 0.175 kN cm$^{-2}$, and more preferably at least about 0.2 kN cm$^{-2}$, at a solid fraction representative of the tablet. The disclosure thereof is concentrated to provide a composition with sufficient hardness yield during a high-speed tabletting operation, in particular to resist erosion during application of a coating layer. According to a preferred embodiment it is provided a pharmaceutical composition in a form of an orally deliverable tablet having a core comprising pramipexole dihydrochloride monohydrate in an amount of about 0.375, 0.75, 1.5, 3, or 4.5 mg, dispersed in a matrix comprising (a) HPMC type 2208 in an amount of about 35% to about 50% by weight of the tablet and (b) a pregelatinized starch having a tensile strength of at least about 0.15 kN cm$^{-2}$ at a solid fraction of 0.8, in an amount of about 45% to about 65% by weight of the tablet; said core being substantially enclosed in a coating that constitutes about 2% to about 7% of

EXTENDED RELEASE PELLET FORMULATION CONTAINING PRAMIPEXOLE OR A PHARMACEUTICALLY ACCEPTABLE SALT THEREOF

This application is a continuation of U.S. Ser. No. 12/276,610, filed Nov. 24, 2008; U.S. Ser. No. 12/276,610 is a continuation of U.S. Ser. No. 11/202,689, filed Aug. 12, 2005.

RELATED APPLICATIONS

This application claims priority to European Application No. 04019249.4 filed Aug. 13, 2004, which is hereby incorporated by reference in its entirety.

FIELD OF THE INVENTION

The present invention is directed to an extended release pellet formulation containing pramipexole or a pharmaceutically acceptable salt thereof, method for manufacturing the same and use thereof.

BACKGROUND OF THE INVENTION

Pramipexole is a known dopamine D2 receptor agonist. It is structurally different from the ergot-derived drugs, e.g., bromocriptine or pergolide. It is also pharmacologically unique in that it is a full agonist and has receptor selectivity for the dopamine D2 family of dopamine receptors.

Pramipexole is designated chemically as (S)-2-amino-4,5,6,7-tetrahydro-6-(propylamino)benzothiazole and has the molecular formula $C_{10}H_{17}N_3S$ and a relative molecular mass of 211.33. The chemical formula is as follows:

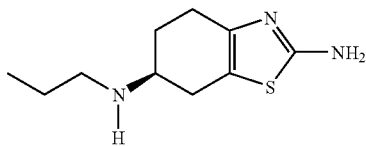

The salt form commonly used is pramipexole dihydrochloride monohydrate (molecular formula $C_{10}H_{21}Cl_2N_3OS$; relative molecular mass 302.27). Pramipexole dihydrochloride monohydrate is a white to off-white, tasteless, crystalline powder. Melting occurs in the range of 296° C. to 301° C., with decomposition. Pramipexole is a chiral compound with one chiral center. Pure (S)-enantiomer is obtained from the synthetic process by chiral recrystallization of one of the intermediates during synthesis.

Pramipexole dihydrochloride monohydrate is a highly soluble compound. Water solubility is more than 20 mg/mL and solubility in buffer media is generally above 10 mg/ml, between pH 2 and pH 7.4. Pramipexole dihydrochloride monohydrate is not hygroscopic, and has a highly crystalline nature. Under milling, the crystal modification (monohydrate) does not change. Pramipexole is very stable in the solid state, yet in solution it is light sensitive.

Pramipexole immediate release (IR) tablets were first authorized in the USA in 1997, followed over the course of the next years by marketing authorizations in the European Union (EU), Switzerland, Canada, and South America as well as in countries in Eastern Europe, the Near East, and Asia.

Pramipexole IR tablets are indicated in the EU and US for the treatment of signs and symptoms of either early Parkinthe weight of the tablet, said coating comprising an ethyl cellulose-based hydrophobic or water-insoluble component and an HPMC-based pore-forming component in an amount of about 10% to about 40% by weight of the ethyl cellulose-based component.

Furthermore, WO 2004/010999 discloses an orally deliverable pharmaceutical composition comprising a therapeutically effective amount of pramipexole or a pharmaceutically acceptable salt thereof and at least one pharmaceutically acceptable excipient, said composition exhibiting at least one of (a) an in vitro release profile wherein on average no more than about 20% of the pramipexole is dissolved within 2 hours after placement of the composition in a standard dissolution test; and (b) an in vivo pramipexole absorption profile following single dose oral administration to healthy adult humans wherein the time to reach a mean of 20% absorption is greater than about 2 hours and/or the time to reach a mean of 40% absorption is greater than about 4 hours. However, in practical use, it appears that any formulation having a modified or controlled release profile designed for a once daily application would meet the above requirements for which a general teaching how to adjust such a profile is missing. All examples are directed to tablets and not to coated pellets.

Absorption profile in vivo with matrix systems is frequently highly variable due to differences in gastrointestinal transit times. Multiparticle extended release formulations such as pellets distribute in the gastrointestinal tract and therefore show reduced variability in rate and extent of absorption. Furthermore different dose strengths can be achieved easily by filling different amounts of the same extended release pellet type into capsules. As reproducible absorption is mandatory with pramipexole and there is a wide range of therapeutic dose strengths, these properties offer considerable advantages of pramipexole extended release pellets over the predescribed examples mentioned above.

Therefore, it is an object of the present invention to provide an extended release pellet formulation of pramipexole or a pharmaceutically acceptable salt thereof which may be filled in a capsule and is suitable for once-daily oral administration. It is a further object to provide a pellet formulation comprising pramipexole or a pharmaceutically acceptable salt thereof which may be filled in a capsule and is suitable to provide a day-long therapeutic effect and will allow patients to treat their symptoms with a single daily dose, and makes it possible to adjust the release profile of the active ingredient according to a selected release profile dependent or independent from the pH value. Furthermore, a method of manufacturing the pellet formulation shall be provided.

DESCRIPTION OF THE INVENTION

Surprisingly, it has been found that pramipexole or a pharmaceutically acceptable salt thereof may be used in formulations as once daily extended (or slow) release pellets and two alternative formulation principles allow different release rate types dependent or independent from the pH value.

One embodiment of the present invention relates to an extended release pellet comprising an active ingredient selected from pramipexole and the pharmaceutically acceptable salts thereof, and at least one release-modifying excipient.

Preferably the invention relates to an extended release pellet, wherein the active ingredient is embedded within a matrix formed by the at least one release-modifying excipient, which is preferably selected from the group of lipids, waxes, and water-insoluble polymers.

Also preferred is an extended release pellet comprising a core and a coating, wherein at least one release-modifying excipient is incorporated in the coating.

Also preferred is an extended release pellet, wherein the active ingredient is incorporated in the core.

Also preferred is an extended release pellet, wherein the coating comprises at least a first layer and a second layer surrounding the first layer, wherein the first layer comprises the active ingredient, and wherein the second layer comprises at least one release-modifying excipient, preferably selected from ethyl cellulose, cellulose acetate, polyvinylacetate, polyacrylates, polymethacrylates, and ammonio methacrylate copolymer.

Most preferred is an extended release pellet, wherein the second layer further comprises at least one water-soluble excipient, preferably selected from hydroxypropyl cellulose, hydroxypropyl methyl cellulose, polyvinylpyrrolidone, and polyethylene glycol.

Particularly preferred is an extended release pellet, wherein the second layer further comprises an enteric-coating polymer, preferably selected from methacrylic acid copolymers type A and B.

Particularly preferred is an extended release pellet, wherein the second layer comprises from about 10 to about 85 wt.-% of the enteric-coating polymer and from about 15 to about 75 wt.-% of the water-insoluble polymer.

More particularly preferred is an extended release pellet, wherein the core comprises a saccharide, such as saccharose, starch, cellulose, and a cellulose derivative, preferably microcrystalline cellulose.

In a further embodiment the present invention relates to an extended release pellet formulation comprising:
  an inert pellet core;
  a first layer being an active ingredient layer comprising pramipexole or a pharmaceutically acceptable salt thereof and optionally one or more wet binders and other excipients; and
  a second layer provided on the first layer, the second layer being an extended release coating comprising:
    (a) at least one water-insoluble polymer and optionally a pore former, the resulting pellet having a pH-independent in vitro release characteristic, or
    (b) a mixture of a pH-dependent enteric-coating polymer and a pH-independently water swelling polymer, the resulting pellet having a close to zero order in vitro release characteristic at acidic pH values up to pH 6.8, an accelerated release above pH 6.8 and a more accelerated release above pH 7.3.

The expression "layer" should be understood in its broadest sense also including a coating or a film or any kind of (partly or fully) surrounding material used in the pharmaceutical sector and having a defined thickness.

Instead of using an inert pellet core and a first layer of active principle, pellets can also be formed by extrusion of active principle together with excipients in a wet extrusion or melt extrusion process.

The extended release formulations (a) and (b) according to the present invention intended for oral administration allow to select and estimate which in vitro release characteristic and timing of a formulation is most suitable to achieve the desired in vivo plasma profiles preferably with a once daily application. Therefore, two different formulation principles have been developed for pellets. The two formulation principles have different release rate types and a different pH dependency is available. These alternative formulations are beneficial to patients as the extended release drug delivery will allow patients to treat their symptoms with a single daily dose, thereby increasing patient convenience and compliance.

The term "in vitro release characteristic" as used hereinbefore or hereinafter is directed to a release characteristic as obtained in a kind of normally used liquid medium for in vitro experiments wherein the release of active ingredient from the extended release formulation can occur, i.e., for example, in in vitro dissolution media, but also in body fluids or simulated body fluids, more in particular in the gastrointestinal fluids.

In the frame of the present invention the term "extended" release should be understood in contrast to an immediate release, the active ingredient is gradually, continuously liberated over time, sometimes slower or faster, dependent or independent from the pH value. In particular, the term indicates that the formulation does not release the full dose of the active ingredient immediately after oral dosing and that the formulation allows a reduction in dosage frequency, following the definition for extended release, interchangeable with slow release. A slow or extended release dosage form is used synonymously with prolonged action, sustained release, or modified release dosage form. Preferably the extended release dosage form allows at least a two-fold reduction in dosing frequency or a significant increase in patient compliance or therapeutic performance as compared to that presented as a conventional dosage form (e.g., as a solution or a prompt drug-releasing, conventional solid dosage form).

According to the teaching of the present invention two types of extended release pellet formulations are available showing different in vitro release characteristics. The two types have the same structure, i.e., an inert pellet core and a first and a second layer applied thereon in this order, the first layer represents the active ingredient layer comprising pramipexole or a pharmaceutically acceptable salt thereof and optionally a binder and further excipients, the second layer represents a functional coating either comprising a water-insoluble polymer with a pore former or a mixture of an enteric-coating polymer, i.e., which is resistant against gastric juice, and a non-dissolving water swelling polymer.

According to the present invention under "formulation (a)" is understood the pellet formulation having the second layer as above-defined under (a) and under "formulation (b)" is understood the pellet formulation having the second layer as above-defined under (b) whereas the inert pellet core and first layer compositions of formulation (a) and (b) will be the same.

The extended release pellet formulation (a) of the present invention applies a water-insoluble polymer preferably with a pore former in the second layer leading to an exponential ($1^{st}$ in vitro release characteristic, which is widely independent of the pH value. The extended release pellet formulation (b) of the present invention applies a mixture of a pH-dependent enteric-coating polymer and a pH-independently water swelling polymer, the resulting layer having a close to zero order in vitro release characteristic over a broad period of time at acidic pH values up to pH 6.8, an accelerated release above pH 6.8 and an more accelerated release above pH 7.3. In addition to the close to zero order release for the main portion of drug, the latter is furthermore characterized by a certain lag time until drug release becomes substantial and, after the main portion of drug is released, by a flattening of the release profile until an asymptote is reached. This results in a sigmoid profile, i.e., an S-shaped dissolution profile.

A close to zero order in vitro release characteristic indicates a curve which has a virtually constant ascending slope.

The inert pellet core present in both alternate pellet formulations (a) and (b) of the present invention comprises saccharides, preferably polysaccharides, cellulose or a cellulose derivative, starch, and/or waxes. It is preferred if the core consists of or essentially consists of a saccharide, preferably polysaccharide, or cellulose, particularly preferred saccharose or microcrystalline cellulose. Most preferred is microcrystalline cellulose. The size of the cores may be sieve fractions between 0.1 and 3.0 mm, preferably between 0.5 and 1.5 mm.

In case the inert pellet core consists or essentially consists of microcrystalline cellulose it has been found that the thickness of the second layer applied thereon may be decreased to a great extent compared to the use of other core materials, e.g., if the core is composed of saccharose. Therefore, the amount of release controlling polymeric agents and overall spray volumes as well as process times to apply the coating dispersions or solutions may be reduced significantly while the release profile for the active ingredient may be maintained. The related advantages are reducing the amount of excipient and solvent materials used, reducing the process times and the embodiment is cost-saving.

The expression "consisting essentially" is understood in the sense that it does not in principle exclude the presence, in addition to the mandatory components mentioned, of other components, the latter can be excipients, the presence of which does not affect the essential nature of the formulation.

According to pellet formulations (a) and (b) of the present invention there is provided a first layer or coating on the inert core pellet comprising pramipexole or a pharmaceutically acceptable salt thereof and optionally one or more binders and further excipients. The first layer or coating normally has a thickness of 0.5 to 25 µm, preferably 1 to 5 µm.

As active ingredient pramipexole or a pharmaceutically acceptable salt thereof may be present in any amount suitable for the desired treatment of a patient. A preferred salt of pramipexole is the dihydrochloride salt, most preferably in the form of the monohydrate. Usual amounts are from about 0.1 to about 5 mg pramipexole salt. According to a preferred embodiment, e.g., 0.750 mg pramipexole dihydrochloride monohydrate, corresponding to 0.524 mg anhydrous base, is used in the extended release capsule or tablet formulation according to the present invention taking into account that all pellets which are filled in a capsule or compressed into a tablet are to give the desired dose strengths. Preferably the extended release pellets are filled into hard capsules, but also compressing of the pellets together with further excipients into tablets is possible.

However, any other amount of active ingredient suitable for treatment may be used with the only proviso that the amount of pramipexole or salt, that is the whole number of pellets being present in one capsule, is sufficient to provide a daily dose in one to a small plurality, for example one to about 4, of capsules to be administered at one time. Preferably the full daily dose is delivered in a single capsule. An amount of pramipexole salt, expressed as pramipexole dihydrochloride monohydrate equivalent, of about 0.1 to about 10 mg per capsule, or about 0.05% to about 5% by weight of the composition, will generally be suitable. Preferably an amount of about 0.2 to about 6 mg, more preferably an amount of about 0.3 to about 5 mg, per capsule is present. Specific dosage amounts per capsule, e.g., include 0.375, 0.5, 0.75, 1.0, 1.5, 3.0, and 4.5 mg pramipexole dihydrochloride monohydrate. The amount that constitutes a therapeutically effective amount varies according to the condition being treated, the severity of said condition, and the patient being treated.

The binder(s) present in the first layer may be any suitable wet binder(s) as used in the pharmaceutical sector. Examples are hydrophilic polymers which may swell and glue upon contact with water. The viscosity of the polymers preferably ranges from 1 to 1,000 mPa·s (apparent viscosity of a 2% aqueous solution at 20° C.). Examples of such polymers are alkylcelluloses, such as, methyl cellulose; hydroxyalkylcelluloses, for example, hydroxymethyl cellulose, hydroxyethyl cellulose, hydroxypropyl cellulose and hydroxybutyl cellulose; hydroxyalkyl alkylcelluloses, such as, hydroxyethyl methyl cellulose and hydroxypropyl methyl cellulose; carboxyalkylcelluloses, such as, carboxymethylcellulose; alkali metal salts of carboxyalkylcelluloses, such as, sodium carboxymethylcellulose; carboxyalkylalkylcelluloses, such as, carboxymethyl ethyl cellulose; carboxyalkylcellulose esters; other natural, semisynthetic, or synthetic polysaccharides, such as, alginic acid, alkali metal and ammonium salts thereof, carrageenans, galactomannans, tragacanth, agar-agar, gum arabicum, guar gum, xanthan gum, starches, pectins, such as sodium carboxymethylamylopectin, chitin derivates such as chitosan, polyfructans, inulin; polyacrylic acids and the salts thereof; polymethacrylic acids and the salts thereof, methacrylate copolymers; polyvinyl alcohol; polyvinylpyrrolidone, copolymers of polyvinylpyrrolidone with vinyl acetate; combinations of polyvinyl alcohol and polyvinylpyrrolidone; polyalkylene oxides such as polyethylene oxide and polypropylene oxide and copolymers of ethylene oxide and propylene oxide.

Preferable binders are polysaccharides, in particular cellulose derivatives and more preferred cellulose ether derivatives. A most preferred cellulose ether derivative is hydroxypropyl cellulose.

Different viscosity grades of hydroxypropyl cellulose and hydroxypropyl methylcellulose are commercially available. Hydroxypropyl methyl cellulose preferably used as a wet binder in the present invention has a viscosity grade ranging from about 3 mPa·s to about 1,000 mPa·s, in particular ranging from about 3 mPa·s to about 20 mPa·s and preferably a viscosity grade of about 4 mPa·s to about 18 mPa·s (apparent viscosity of a 2% aqueous solution at 20° C.), e.g., hypromellose 2910 (DOW, Antwerp, Belgium).

Hydroxypropyl cellulose having a viscosity lower than 1,500 mPa·s (apparent viscosity of 1% aqueous solution at 20° C.) is preferred, in particular hydroxypropyl cellulose having a viscosity in the range from about 75 to about 150 mPa·s (5% aqueous solution), preferably from 300 to 600 mPa·s (10% aqueous solution), e.g., KLUCEL® EFO (Hercules, Wilmington, USA).

Preferably, the amount of binder in the first layer of the pellet formulations (a) and (b) of the present invention ranges from 0 to about 30% by weight, preferably from about 10 to about 20% by weight. Also, a combination of binders may be used.

According to a preferred embodiment of the present invention the first layer of the extended release pellet formulation of alternatives (a) and (b) comprises or consists of hydroxypropyl cellulose, pramipexole or a pharmaceutically acceptable salt thereof and excipients. The amount of hydroxypropyl cellulose is preferably in the range from 1 to 30, particularly preferred from 5 to 25, most preferred from 10 to 20% by weight. The amount of excipients is preferably in the range from 1 to 40, particularly preferred from 2 to 25, most preferred from 5 to 15% by weight.

Beside pramipexole or a salt thereof, and the binder(s), the first layer or coating of both formulations (a) and (b) of the present invention may also optionally comprise excipients, i.e., pharmaceutically acceptable formulating agents, in order to promote the manufacture and coating properties of the preparation. These formulating agents comprise, for example, glidants, antiadherents, binding agents, granulating agents, anti-caking agents, and lubricants. Other conventional excipients known in the art can also be included.

A glidant and antiadherent can be used to improve the manufacturing during the spray process and to prevent sticking and picking of the pellets to each other. Suitable glidants include colloidal silicon dioxide, magnesium trisilicate, powdered cellulose, starch, talc, tribasic calcium phosphate and the like. In a preferred embodiment, talc is included as a glidant/antiadherent in an amount up to about 25%, preferably about 5% to about 15%, by weight of the first layer.

According to the present invention waxes, lipids, and water-insoluble polymers may be used as release modifying agents.

Suitable waxes include compounds that are chemically defined as esters of fatty acids and fatty alcohols or sterols, as well as derivatives and functional analogues thereof. Usually, the chain length of the fatty acid moiety is at least about 8 carbon atoms, and more typically at least about 12 carbon atoms. Waxes are plastic solids at room temperature, but very often have a moderately low melting point, such as below about 80° C.-100° C. Waxes are usually somewhat more brittle than solid fats, and less greasy. More recently, also compounds which are chemically different from this definition but similar in their properties have been referred to as waxes. These waxes or functional analogues may also be used according to the present invention. Examples of potentially suitable waxes and wax analogues include white and yellow beeswax, carnauba wax, microcrystalline wax, spermaceti wax, candellila wax, saturated fatty acid esters, sugar cane wax, paraffin wax, castor wax, and wax mixtures such as nonionic or anionic emulsifying wax, cetyl esters wax, and lanolin. Among the presently preferred waxes are beeswax, carnauba wax, saturated fatty acid esters, and microcrystalline wax.

Suitable lipids include lipophilic compounds or mixtures of natural or synthetic origin that have similar properties as glycerides and other natural lipids, such as phospholipids, sphingolipids, ceramides, sterols, steroids, and carotenoids. Lipids may be solid or liquid at room temperature, and may be viscous in their liquid state. Preferably, a lipid used to carry out the invention is solid at room temperature, even though a liquid lipid may also be used in mixtures, such as in a mixture with a solid lipid or wax. Examples of lipids which may be found useful include mono-, di-, and glycerides of saturated or unsaturated fatty acids, such as—optionally hydrated or partially hydrated—vegetable oils (e.g., peanut, castor, coconut, cottonseed, palm, or soybean), edible fat, hard fat, glyceryl behenate, glyceryl stearate, glyceryl palmitate; fatty acids such as stearic acid, behenic acid, palmitic acid, oleic acid, lauric acid, myristic acid, arachidic acid, linolenic acid, linoleic acid, arachidonic acid, and erucic acid; fatty alcohols such as those corresponding to the previously mentioned fatty acids, in particular cetyl alcohol, stearyl alcohol, oleyl alcohol, and palmityl alcohol; glycerides, fatty acids, or fatty alcohols which are modified with sorbitan or polyoxyethylene; and phospholipids such as lecithin or phosphatidylcholine. Particularly suitable lipids are solid or at least partially hydrated triglycerides including edible fat, hard fat, hydrated peanut-, castor-, coconut-, cottonseed-, palm-, and soybean oil, glyceryl behenate, glyceryl stearate, glyceryl palmitate, stearic acid, behenic acid, and palmitic acid.

Suitable water-insoluble polymers may comprise the water-insoluble polymers as defined below for the formulations according to the present invention.

Among the optional formulating agents that further may be comprised in the pellet formulation there may be mentioned agents such as polyvidone; starch; acacia gum; gelatin; seaweed derivatives, e.g., alginic acid, sodium and calcium alginate; cellulose, preferably microcrystalline cellulose, cellulose derivatives, e.g., ethyl cellulose, hydroxypropyl methyl cellulose, having useful binding and granulating properties.

According to the pellet formulation (a) of the present invention the second layer is provided on the first layer, the second layer, a functional layer, being an extended release coating or film coating comprising at least one water-insoluble polymer and preferably a pore former, the resulting pellet having an pH-independent in vitro release characteristic. Therefore, the second layer is a non soluble diffusion lacquer with pores leading to an exponential ($1^{st}$ order) release profile of the pellet formulation (a) which has practically a pH-independent in vitro release characteristic. A release characteristic which is pH-independent indicates that the release characteristic is virtually the same in different pH media.

The water-insoluble polymer according to the present invention is defined as a polymer having a water solubility which is lower than 1 part soluble in 1,000, preferably lower than about 1 part soluble in 10,000 parts of solvent.

The release-controlling second layer, coating or film according to pellet formulation (a) comprises one or more hydrophobic or water-insoluble polymers such as cellulosic polymers e.g., methyl cellulose, ethyl cellulose, hydroxyethyl cellulose, cellulose esters such as cellulose acetate, polyvinyl acetate, polymers and copolymers of acrylic acid and methacrylic acid and esters thereof, such as ammonia methacrylate copolymer, type B, and the like. Particularly preferred is ethyl cellulose.

The hydrophobic or water-insoluble component, preferably ethylcellulose, typically constitutes about 1% to about 25%, preferably about 3% to about 10%, by weight of the pellet as a whole, provided that microcrystalline cellulose pellets are used as described above. In case sugar pellets are used higher amounts of ethylcellulose can become necessary.

The second layer can contain one or more pore formers, such as more water soluble polymers, like hydroxypropyl cellulose, hydroxypropyl methyl cellulose, and highly water soluble polymers, like polyvinyl pyrrolidone and polyethylene glycol, or other water soluble excipients, such as lactose and mannitol. Particularly preferred pore formers are polyethylene glycols (e.g., Macrogol 6000). The amount of pore former is suitably up to 40 percent by weight of the layer, coating or film, preferably up to 25% by weight. Pore formers like polyethylene glycols also serve as plasticizers, i.e., the function of such excipients either as plasticizer and/or pore former can not be clearly differentiated.

The second layer can optionally contain additional pharmaceutically acceptable excipients as mentioned above, preferably used are plasticizers, dyes and antiadherents. Particularly preferred plasticizers are polyethylene glycols (e.g., Macrogol 6000), triacetin, and triethylcitrate. The amount of plasticizer is suitably up to 25 percent by weight of the layer, coating or film. Anti-adherents, such as talc and magnesium stearate can be used.

The extended release pellet formulation according to formulation (a) is pH-independent, Therefore, the disadvantage that food related dose-dumping which may be encountered is avoided. The problem of food related dose-dumping in fed patients can be attributed to a lot of factors such as the mechanical forces that are exerted by the stomach on its content and thus on an ingested preparation as well as the different pH regions of the gastrointestinal tract. Since the pH values encountered in the gastrointestinal tract vary not only with the region of the tract, but also with the intake of food, an extended release formulation preferably also has to provide a controlled release profile and in particular has to avoid dose-dumping regardless whether the patient is in fasted or fed conditions.

Therefore, the oral extended release formulation (a) according to the present invention retains its pharmacokinetic release profile along its way through the gastrointestinal tract so as to avoid undesirable fluctuations in drug plasma concentrations or complete dose-dumping, in particular avoids dose-dumping in different regions of the gastrointestinal tract.

The alternate pellet formulation (b) has the same structure with regard to the inert pellet core and first layer composition as defined for formulation (a) but a different second layer or functional film coating composition. Thus, the second layer of formulation (b) comprises or essentially consists of a mixture of a pH-dependent enteric-coating polymer and a pH-independently water swelling polymer, the resulting pellet having a close to zero order in vitro release characteristic at acidic pH values up to pH 6.8, an accelerated release above pH 6.8 and a more accelerated release above pH 7.3.

The pH-dependent enteric-coating polymer is preferably an anionic polymer, more preferably an anionic carboxylic acrylic polymer soluble above a pH value of 5.5, preferably above a pH value of 7.0. By an anionic polymer is meant a polymer containing anionic groups after dissociation depending on pH. For the purpose of this invention such polymer should be soluble above pH 5.5, preferably above pH 7.0. Preferably the anionic carboxylic acrylic polymer is selected from partly methyl esterified methacrylic acid polymers. Suitable partly methyl esterified methacrylic acid polymers are sold under the names EUDRAGIT® L and EUDRAGIT® S, preferably used are EUDRAGIT® S100 and L100.

The water-insoluble, pH-independent swelling polymer is preferably selected from quaternary ammonium substituted acrylic polymers. Such polymers are sold under the names EUDRAGIT® RS and EUDRAGIT® RL having an ammonium substitution of about 5 and about 10 percent by weight, respectively. Preferably EUDRAGIT® RS 100 is used.

It is especially preferred if the layer or film coating comprises the enteric-coating polymer such as the anionic carboxylic acrylic polymer in an amount of 10 to 85 percent by weight of the layer or coating and the water-insoluble, pH-independent swelling polymer, selected from quaternary ammonium substituted acrylic polymers, in an amount of 15 to 75 percent by weight of the layer or coating. Depending on the amount and ratio of polymers processed in the preparation, the release profile can be tuned with regard to the release rate, that is the time to, e.g., reach a level of 50% of drug dissolved, and with regard to the extent of pH dependency. In general, an excess of the anionic carboxylic acrylic polymer, e.g., EUDRAGIT® S 100, over the quaternary ammonium substituted acrylic polymers is required to achieve the desired accelerated dissolution characteristic at a pH above 6.8, The second layer, coating or film normally has a thickness of 5 to 80 μm, preferably 20 to 60 μm.

The second functional layer according to formulation (b) of the present invention takes advantage of the fact that the time of passage through the small intestine is rather constant, said time is about 2 to 5 hours. According to the invention the change of pH from acid to about neutral at the pylorus is employed as a trigger mechanism changing the physical condition of the layer and finally causing the accelerated release of the active substance. Therefore the formulation releases a major part of its drug contents in the small intestine, and in the lower part of the intestinal system preferentially in the large intestine, i.e., the colon. With a layer or coating according to formulation (b) the release of pramipexole or a pharmaceutically acceptable salt thereof can be accelerated in the lower parts of the intestine, that is under conditions of higher physiological pH, thereby reducing the loss in bioavailability and increase in variability typically observed with pH independent release systems in situations of shorter gastrointestinal transit times According to a preferred embodiment of the present invention a pore-forming component may be present in the second layer or film coating of formulation (b). The pore-forming component may be selected from the group consisting of water soluble polymers, such as polyethylene glycols, polyvinyl pyrrolidone, and cellulose derivatives, such as hydroxypropyl cellulose and hydroxypropyl methyl cellulose, preferably hydroxypropyl cellulose. The pore-forming component is typically present in an amount of about 1% to about 25%, preferably about 2% to about 10%, by weight of the polymer mixture in the second layer.

A particular preferred pore-forming component is hydroxypropyl cellulose having a viscosity in the range from about 150 to about 700 mPa·s, preferably from 200 to 600 mPa·s, e.g., selected from the KLUCEL® series such as KLUCEL® EF or LF (Hercules, Wilmington, USA).

The polymer pore-forming component forms diffusion pores and leads to an accelerated hydration and an altering of the rebuffering characteristics of the layer or film coating with a change from acid to alkaline medium and results in an accelerated penetrability of the layer or coating for the active ingredient pramipexole or its salt in the pH range >7.3

Therefore, the presence of a pore forming component provides the further advantage that the release characteristic is accelerated and occurs more rapid, i.e., the effects of the second layer are enhanced significantly.

According to a preferred embodiment an extended release pellet formulation has the following composition:

Inert Pellet Core
90 to 100% by weight of saccharose or microcrystalline cellulose; and 0 to 10% by weight of excipient(s)

First Layer
50 to 100% by weight of pramipexole or a salt thereof; 0 to 30% by weight of binder(s); and 0 to 50% by weight of excipient(s)

Second Layer
50 to 99% by weight of water-insoluble polymer(s); and 1 to 50% by weight of excipient(s) or a mixture of:
10 to 85% by weight of a pH-dependent enteric-coating polymer; 15 to 75% by weight of a pH-independently water swelling polymer; and 1 to 50% by weight of excipient(s).

The first and second layers or coatings should be applied at as uniform a thickness as possible to provide optimum control of release rate of the pramipexole or pramipexole salt.

If pellets are formed by extrusion, the following compositions are most suitable:

Wet Extrusion
Microcrystalline cellulose, powdered cellulose or starch is mixed with pramipexole in ratios delivering the necessary amount of drug in a suitable number of pellets with regard to reproducibility of filling and acceptable capsule size. Extrusion is achieved by addition of water only or of water containing binders such as povidone or methyl cellulose, hydroxypropyl cellulose. In order to achieve the desired release rates, other excipients such as lactose, microcrystalline cellulose, starch, etc., can be added.

Melt Extrusion
Melt extrusion is achieved either by hydrophilic or lipophilic compounds with melting points between 40° C. and 120° C. Suitable examples are polyethylene glycol 2000-10000, poloxamer 188, carnauba wax, hydrogenated castor oil, stearyl alcohol, cetyl alcohol and mixtures thereof. In order to achieve the desired release rates, other excipients such as lactose, microcrystalline cellulose, starch, etc., can be added.

These pellets are then coated by retarding lacquers as described for the pellets consisting of inert starters with drug layers sprayed onto them.

Some excipients are suitable also to achieve extruded pellets with suitable extended release even without retarding lacquers. These are, e.g., carnauba wax, hydrogenated castor oil and mixtures thereof for lipophilic pellets or carbopol, anionic carboxylic acrylic polymer, e.g., partly methyl esterified methacrylic acid polymers. Suitable partly methyl esterified methacrylic acid polymers are sold under the names EUDRAGIT® L and EUDRAGIT® S, preferably used are EUDRAGIT® S100 and L100.

The extended release pellets can be of sizes between 0.2 and 3 mm in diameter, preferably between 0.5 to 1.5 mm, most preferred between 0.7 and 1.0 mm. According to the present invention the pellets are preferably filled in hard capsules. The extended release capsules can be of any size and shape and color, e.g., for a 0.75 mg dose strengths preferably a size 3 capsule can be used. The capsule shell is usually made from hydroxypropyl methyl cellulose (so-called HPMC or vegetable capsules) or gelatin. The capsules according to the present invention are usually filled with pellets, for example, more than 150 extended release pellets. Each pellet is built up of an inert (starter) core pellet, an active ingredient layer and an extended or slow release film coating. In one capsule, the amount of pramipexole or the pharmaceutically acceptable salt thereof contained in the pellets may preferably be sufficient to provide a daily dose administered at one time.

Alternatively the extended release pellets can be admixed with fillers and binders, such as microcrystalline cellulose, carrageenans, and alginates and disintegrants, such as sodium starch glycolate, sodium carboxymethyl cellulose (croscarmellose), further excipients, like glidants and lubricants, and be compressed into tablets.

The present invention is further directed to the use of the extended release pellet formulation or capsule according to the present invention for preparing a medical composition for the treatment of Parkinson's Disease and complications or disorders associated therewith.

According to the present invention it is also provided a method of manufacturing the extended release pellet formulation comprising the steps of
(1) providing an inert starter pellet core;
(2) applying a solution or dispersion of a first coating composition comprising pramipexole or a pharmaceutically acceptable salt thereof, optionally a binder and further excipient(s) onto the inert starter pellet core, preferably by spraying the solution/dispersion of the coating composition onto the inert starter pellet core, wherein the active ingredient in form of pramipexole or a pharmaceutically acceptable salt thereof is used as unmilled or milled material, dissolved/dispersed in a solvent together with the optional binder(s) and excipient(s) and sprayed onto the inert starter pellet core and subsequently drying the obtained active ingredient pellet; and
(3) applying a solution or dispersion of a second coating composition as functional coating composition onto the active ingredient pellet obtained in step (2), preferably by spraying the coating solution/dispersion onto the active ingredient pellet wherein the coating composition comprises (a) at least one water-insoluble polymer or (b) a mixture of a pH-dependent enteric-coating polymer and a pH-independently water swelling polymer, and optional excipient(s), and a solvent and subsequently drying the obtained extended release pellet (ER pellet).

Optionally a manual screening after process step (2) and/or process step (3) may be performed in order to remove agglomerates.

The solvents employed according to the process of the invention are solvents having a sufficient volatility to evaporate under the conditions of application, leaving a layer of the solute on the surface of the core or body or pellet prepared. Organic solvents such as alcohols, hydrocarbons and esters may be used as well as derivatives thereof, such as chlorinated hydrocarbons. Particularly preferred are alcohol such as ethanol or alcohol/water mixtures. The process of applying the coating may be carried out in an apparatus normally used in the pharmaceutical industry for coating of solid pharmaceutical preparations, preferably in a fluid bed apparatus. The process is normally carried out at 25° C. to 35° C. product temperature, however, temperature and pressure conditions may be varied within broad limits. In a fluid bed spraying process, the temperature of the inlet air is suitably about 20° C. to 60° C.

The obtained extended release pellets are filled in suitable capsules and the capsules of the invention can be packaged in a container, accompanied by a package insert providing pertinent information such as, for example, dosage and administration information, contraindications, precautions, drug interactions and adverse reactions. The capsules are for example filled into High Density Polyethylene (HDPE) bottles. The bottles are closed tightly with screw caps and appropriately labeled. All packaging and labeling activities are performed according to cGMP regulations.

BRIEF DESCRIPTION OF THE DRAWINGS

Referring to FIGS. 1 and 2 a preferred embodiment of the manufacturing process is illustrated with reference to a flow diagram wherein the manufacture of the pellet formulations D, E, F, G, H of Examples 1 to 5 is exemplarily shown. The figures show the detailed process steps of the manufacturing process of the active ingredient pellets (first layer; FIG. 1) and of the slow or extended release pellets (second or functional layer; FIG. 2) and the in process controls performed. FIG. 3 shows the filling of capsules with the obtained pellets.

The manufacturing process described applies to all types of pramipexole extended release pellets and capsules, for example the formulations D, E, F, G, H of Examples 1 to 5, yet there are differences in the qualitative and quantitative composition in some process steps.

Process step (1)—Inert starter pellet core:

In the present embodiment microcrystalline cellulose pellets (Cellets 700) are used which represent the starting material for the subsequent coating step.

Process step (2)—Active ingredient pellets (first coating):

For all types of formulations the same active ingredient pellets with a drug load of 1% (10 mg/g) can serve as starting material for the functional film-coating. Yet also other drug loads in the active ingredient pellets are suitable.

Figure 1:
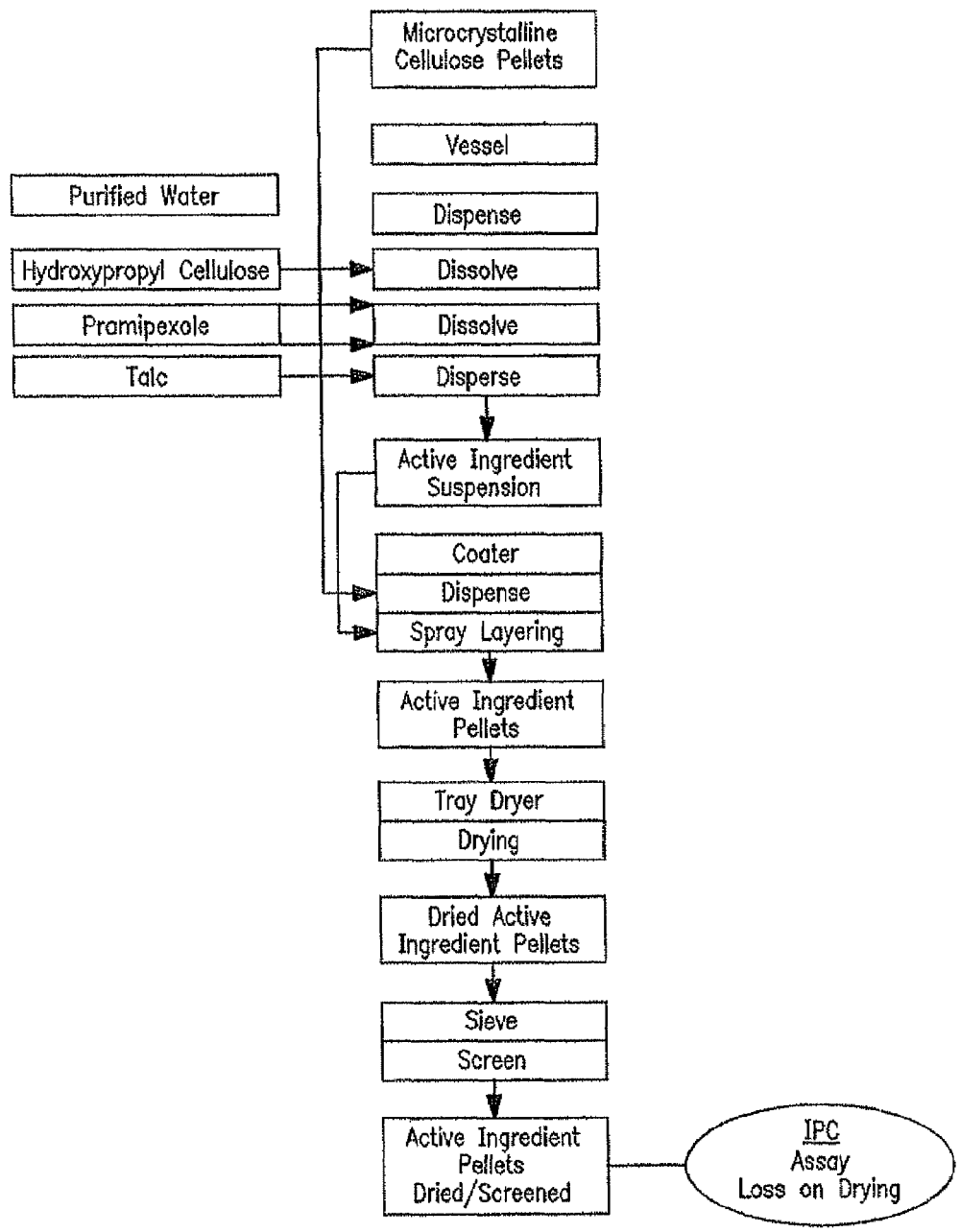
FIG. 1 is a flow diagram illustrating process step (1) of a preferred embodiment of the manufacturing process according to the present invention wherein the first layer is applied on inert starter core pellets.
Figure 2:
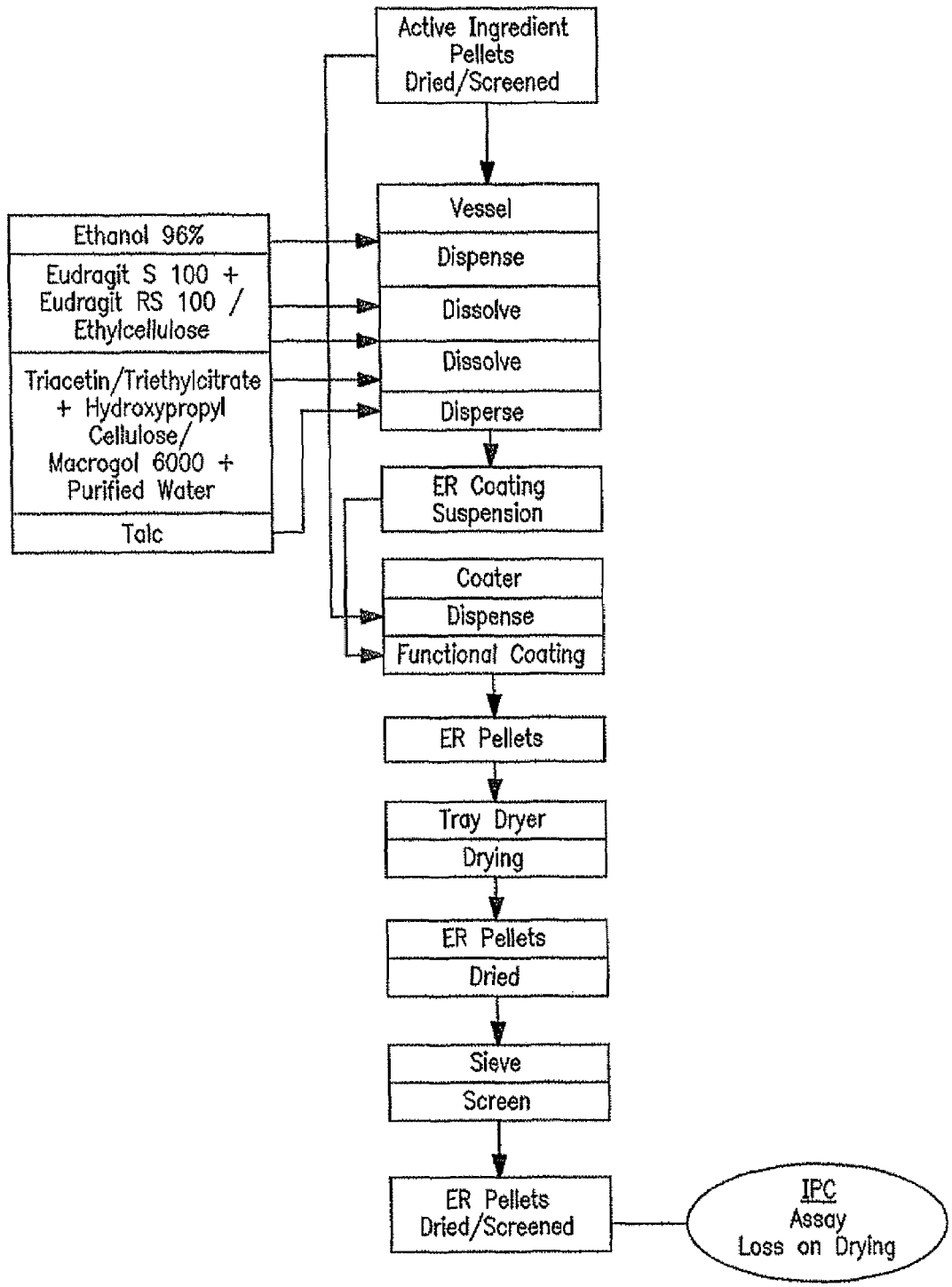
FIG. 2 is a flow diagram illustrating process step (2) of a preferred embodiment of the manufacturing process according to the present invention wherein the second layer is applied on the first layer of the pellets.
Figure 3:
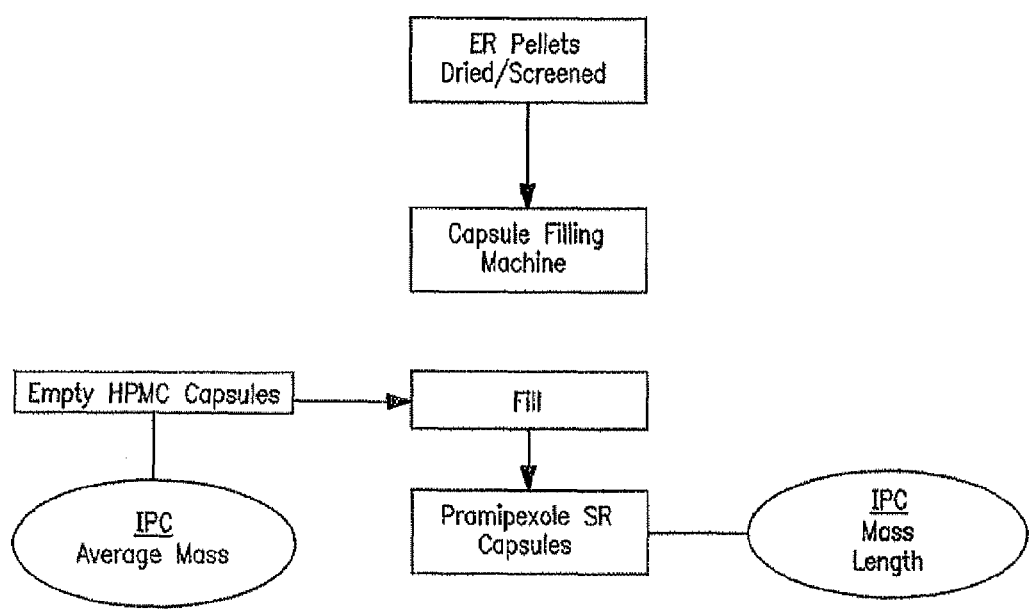
FIG. 3 is a flow diagram illustrating process step (3) of a preferred embodiment of the manufacturing process according to the present invention wherein the pellets are filled in capsules.

According to the present flow chart in FIG. 1, the active ingredient pellets are manufactured by spray-layering of an aqueous solution of pramipexole dihydrochloride monohydrate (active ingredient), unmilled quality, together with hydroxypropyl cellulose (binder) and talc (excipient) onto the surface of microcrystalline cellulose pellets (core, Cellets 700) in a bottom spray fluid bed equipment. Light protection of the spray suspension is normally required. After the spraying is completed, the pellets are dried at 35° C. for 1 hour in a tray dryer. After drying, the pellets are manually screened through a 1.12 mm mesh size screen in order to remove agglomerates.

The in process controls used are: active ingredient assay and loss on drying.

Process step (3)—Functional film coating (second coating):

Depending on the type of formulation (D-H) coating suspensions consisting of methacrylic acid copolymer (type B USP/NF)) and ammonia methacrylate copolymer (type B USP/NF)), or ethyl cellulose, and excipients selected from talc, triacetin or triethylcitrate and hydroxypropyl cellulose or macrogol 6000, are sprayed onto the active ingredient pellets in a bottom spray fluid bed equipment. The solvent used is according to the described embodiment either Ethanol 96% or an Ethanol 96% mixture with water. After the spraying is completed the extended or slow release pellets are dried at 40° C. for 12 to 48 hours in a tray dryer. After drying, the pellets are manually screened through a 1.12 mm mesh size screen in order to remove agglomerates.

The in process controls used are: active ingredient assay and loss on drying.

Process step (4)—Capsule filling (at the example of 0.75 mg dose strength):

An appropriate amount of dried and screened pellets are filled into vegetable capsules (HPMC capsules) or gelatin capsules of size 3 to give the desired dose strengths using a suitable intermittent motion capsule filling machine. The appropriate amount is calculated from the assay result found for the respective batch of slow or extended release pellets.

The in process controls used are: average mass of empty capsules, mass of filled capsule, and length of closed capsule.

Figure 4:
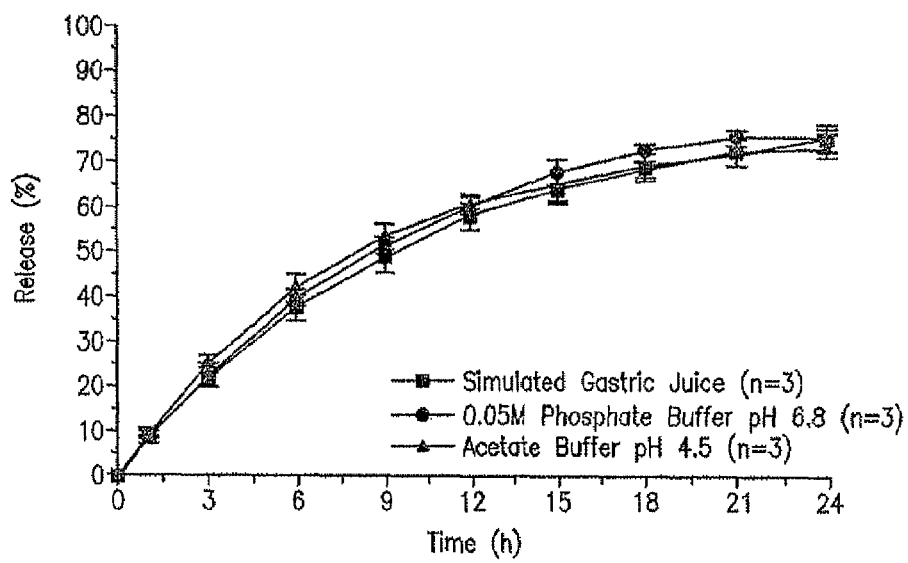
FIG. 4 is a graph illustrating the dissolution profiles of a pellet formulation according to the present invention wherein the second layer is a diffusion lacquer composed of ethyl cellulose (formulation (a)) in 3 different pH media.

Referring to FIG. 4, it represents a graph illustrating the release profiles of a pellet formulation according to the present invention. The pellet contains an inert pellet core, a first layer comprising pramipexole hydrochloride monohydrate and binder and a second layer which represents a diffusion lacquer composed of ethyl cellulose. The detailed composition of the pellet is given in Example 4. The pellet meets the requirements as defined in the abovementioned formulation (a) according to the present invention. The release characteristics of the pellet formulation in 3 different pH media are shown, i.e., in simulated gastric juice, n=3, in 0.05 M phosphate buffer, pH=6.8, n=3 and in acetate buffer, pH=4.5, n=3 (n . . . represents the number of units tested). The value percent of released active ingredient is plotted against the time (hours).

FIG. 4 clearly shows that said pellet formulation has a release characteristic being independent from the pH value.

Figure 5:
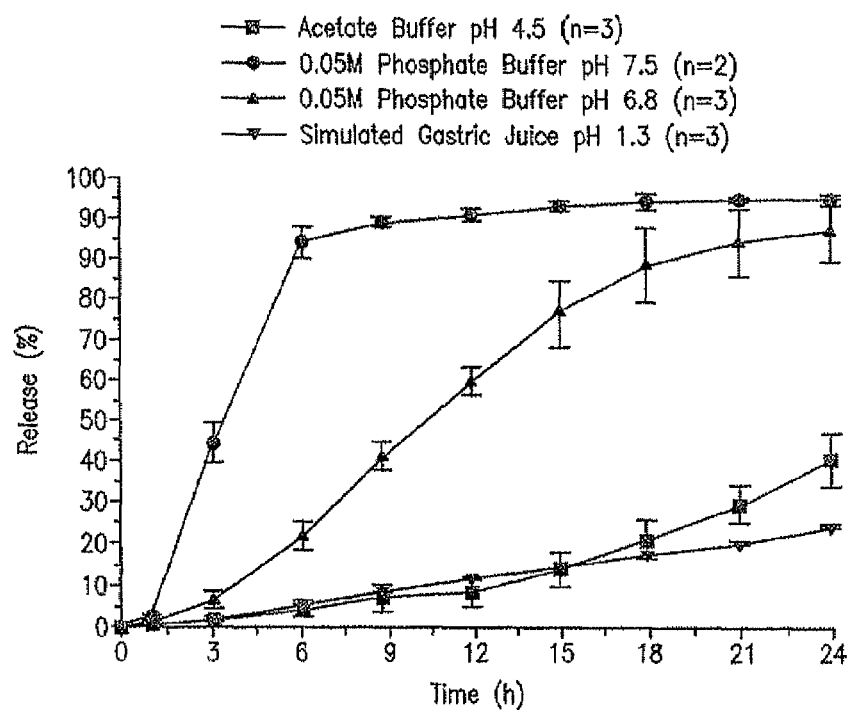
FIG. 5 is a graph illustrating the dissolution profiles of a pellet formulation according to the present invention wherein the second layer is a mixture of EUDRAGIT® S 100 and EUDRAGIT® RS 100 (formulation (b)) in 4 different pH media.

FIG. 5 represents a graph illustrating the release profiles of a pellet formulation according to the present invention. The detailed composition of the pellet is given in Example 2. The pellet formulation has a second layer in accordance with formulation (b) which is composed of a pH-dependent enteric-coating polymer and a pH-independently water swelling polymer (EUDRAGIT® S100/EUDRAGIT® RS 100). The release characteristics of the pellet formulation in 4 different pH media are shown, i.e., in acetate buffer, pH=4.5, n=3, in 0.05 M phosphate buffer, pH=7.5, n=2, in 0.05 M phosphate buffer, pH=6.8, n=3, and in simulated gastric juice, pH=1.3, n=3. The value percent of released active ingredient is plotted against the time (hours).

FIG. 5 clearly shows that the pellet formulation has a release characteristic being dependent from the pH value, i.e., the resulting pellet shows a close to zero order in vitro release characteristic at acidic pH values up to pH 6.8, and an accelerated release at pH 7.5.

Figure 6:
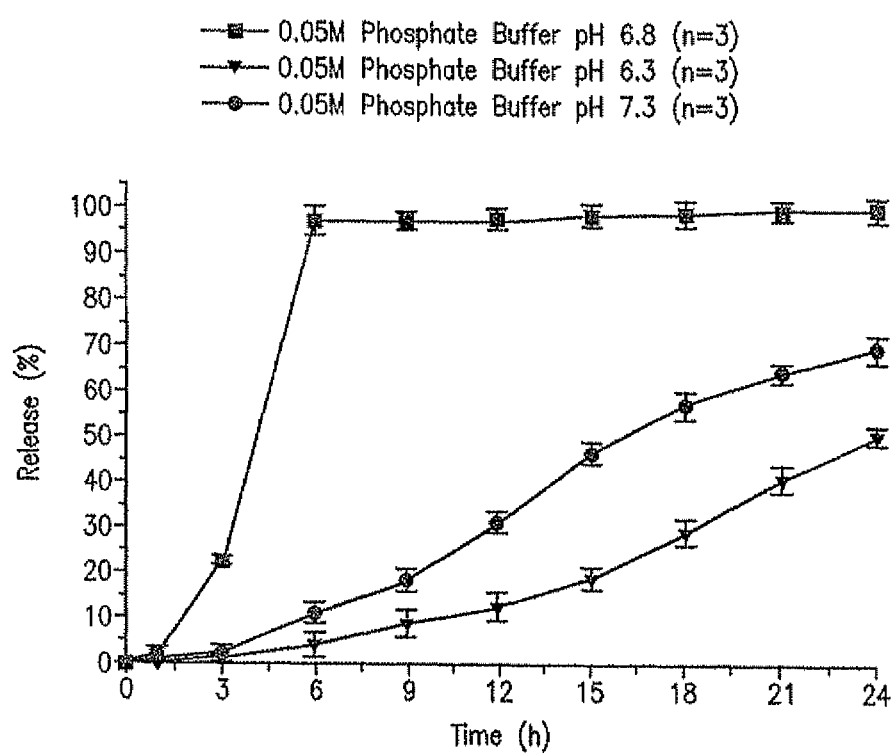
FIG. 6 is a graph illustrating the dissolution profiles of a pellet formulation according to the present invention wherein the second layer is as defined in FIG. 5, but a pore-forming component is additionally present (formulation (b)+pore-forming component) in 3 different pH media.

FIG. 6 represents a graph illustrating the release profiles of a pellet formulation according to the present invention. The detailed composition of the pellet is given in Example 5. The pellet formulation has a second layer in accordance with formulation (b) which is composed of a pH-dependent enteric-coating polymer and a pH-independently water swelling polymer (EUDRAGIT® S100/EUDRAGIT® RS 100) and contains additionally a pore-forming component (KLUCEL® EF) and a plasticizer (triethylcitrate). The release characteristics of the pellet formulation in 3 different pH media are shown, i.e., in 0.05 M phosphate buffer, pH=6.8, n=3, in 0.05 M phosphate buffer, pH=6.3, n=3, and in 0.05 M phosphate buffer, pH=7.3, n=3. The value percent of released active ingredient is plotted against the time (hours).

FIG. 6 clearly shows that the pellet formulation has a release characteristic being dependent from the pH value. The presence of a pore-forming component and the use of a different plasticizer increases and accelerates the effects significantly, compared with the pellet formulation without pore-forming component as shown in FIG. 5.

The advantages of the present invention are manifold:

According to the present invention two types of extended release pellets containing pramipexole or a pharmaceutically acceptable salt thereof are available showing different in vitro release profiles. The two types have the same structure, i.e., an inert starter pellet core and a first layer or coating and second layer or functional film coating provided on the core in this order. The core and first layer or coating are identical and the second layer or coating allows to tune the releasing characteristic as desired.

According to formulation (a) of the present invention at least one water-insoluble polymer is present in the second layer, the resulting pellet having a pH-independent in vitro release characteristic.

According to formulation (b) of the present invention the second layer comprises a mixture of a pH-dependent enteric-coating polymer and a pH-independently water swelling polymer, the resulting pellet having a close to zero order in vitro release characteristic at acidic pH values up to pH 6.8, an accelerated release above pH 6.8 and a more accelerated release above pH 7.3. In the latter case (formulation (b)) the additional presence of a pore-forming component has the significant effect that the release characteristic is enhanced and accelerated compared with the same formulation without a pore-forming component.

Therefore, with a layer or coating according to formulation (b) the extent of release of pramipexole or a pharmaceutically acceptable salt thereof can become more independent of gastrointestinal transit and hence dwell time of the dosage form in the intestine.

It is therefore possible to select a tailor-made release characteristic for patient's needs, symptoms and clinical picture observed, a desired release with a reduced inter- and intraindividual variability of bioavailability.

In case the inert pellet core consists or essentially consists of microcrystalline cellulose, the thickness of the second layer and the amount of release controlling excipients applied thereon may be decreased to a great extent compared to the use of other core materials, e.g., if the core is composed of saccharose.

The primary indication for pramipexole, Parkinson's Disease, is an affliction that becomes more prevalent with advancing age and is often accompanied by decline in memory. Therefore, the pellets according to the present invention providing an extended or slow release of pramipexole or a salt thereof allows to simplify the patient's administration scheme by reducing the amount of recommended daily intakes and improves patient's compliance, particularly relevant for elderly patients. The inventive extended release pellet formulations provide a daily dose administered at one time. The amount that constitutes a therapeutically effective amount varies according to the condition being treated, the severity of said condition, and the patient being treated.

It is further provided a manufacturing process which applies to all types of pramipexole extended release pellets and capsules.

The invention described will now be illustrated by the Examples which follow various other embodiments and will become apparent to the skilled person from the present specification. However, it is expressly pointed out that the Examples and description are intended solely as an illustration and should not be regarded as restricting the invention.

EXAMPLES

In the following Examples cap and body white opaque hydroxypropyl methyl cellulose capsules of size 3 are used, filled with extended release pellets. The complete capsules are intended to be administered orally, and shall not be opened before use. The pramipexole pellets in the Examples contain 0.75 mg of pramipexole dihydrochloride monohydrate, corresponding to 0.524 mg of pramipexole free, anhydrous base.

Example 1

One embodiment of the qualitative and quantitative composition of pramipexole extended release pellets according to the present invention (Formulation D) is shown in Table 1.

TABLE 1

Qualitative and Quantitative Composition of Pramipexole Extended Release (ER) Capsule (Formulation D)

| Ingredient | mg per 0.75 mg capsule | mg per 0.75 mg capsule | Function | Reference to Standards |
|---|---|---|---|---|
| ER Pellets consisting of: | 88.458 | | | |
| Pramipexole dihydrochloride monohydrate | | 0.750 | Active ingredient | Company standard |
| Microcrystalline cellulose pellets (Cellets 700) | | 73.980 | Non-pareille carrier pellet | Ph. Eur./NF |
| Hydroxypropyl cellulose (KLUCEL ® EF) | | 0.150 | Wet binder | Ph. Eur./NF |
| Talc | | 0.495 | Glidant | Ph. Eur./USP |
| Methacrylic acid copolymer, Type B (EUDRAGIT ® S 100) | | 7.500 | Functional coating | Ph. Eur./NF |
| Ammonio methacrylate copolymer, Type B (EUDRAGIT ® RS 100) | | 3.750 | Functional coating | Ph. Eur./NF |
| Triacetin | | 1.833 | Plasticizer | Ph. Eur./USP |
| Ethanol (96%) | | 173.333* | Solvent | Ph. Eur. |
| Purified water | | 30.000* | Solvent | Ph. Eur./USP |
| HPMC capsule, size 3 | 46.000 | | Shell | Company Standard |
| Total | 134.458 | 88.458 | | |

*removed during processing (does not appear in the final product)

Example 2

One embodiment of the qualitative and quantitative composition of pramipexole extended release pellets according to the present invention (Formulation E) is shown in Table 2.

TABLE 2

Qualitative and Quantitative Composition of Pramipexole ER Capsule (Formulation E)

| Ingredient | mg per 0.75 mg capsule | mg per 0.75 mg capsule | Function | Reference to Standards |
|---|---|---|---|---|
| ER Pellets consisting of: | 91.600 | | | |
| Pramipexole dihydrochloride monohydrate | | 0.750 | Active ingredient | Corporate standard |
| Microcrystalline cellulose pellets (Cellets 700) | | 73.980 | Non-pareille carrier pellet | Ph. Eur/NF |
| Hydroxypropyl cellulose (KLUCEL ® EF) | | 0.150 | Wet binder | Ph. Eur./KF |
| Talc | | 0.578 | Glidant | Ph. Eur./USP |
| Methacrylic acid copolymer, Type B (EUDRAGIT ® S 100) | | 9.250 | Functional coating | Ph. Eur./NF |
| Ammonio methacrylate copolymer, Type B (EUDRAGIT ® RS 100) | | 4.625 | Functional coating | Ph. Eur./NF |
| Triacetin | | 2.267 | Plasticizer | Ph. Eur./USP |
| Ethanol (96%) | | 214.167* | Solvent | Ph. Eur. |
| Purified water | | 30.000* | Solvent | Ph. Eur./USP |
| HPMC capsule, size 3 | 46.000 | | Shell | Company Standard |
| Total | 137.600 | 91.600 | | |

*removed during processing (does not appear in the final product)

Example 3

One embodiment of the qualitative and quantitative composition of pramipexole extended release pellets according to the present invention (Formulation F) is shown in Table 3.

TABLE 3

Qualitative and Quantitative Composition of Pramipexole ER Capsule (Formulation F)

| Ingredient | mg per 0.75 mg capsule | mg per 0.75 mg capsule | Function | Reference to Standards |
|---|---|---|---|---|
| ER Pellets consisting of: | 80.063 | | | |
| Pramipexole dihydrochloride monohydrate | | 0.750 | Active ingredient | Corporate standard |
| Microcrystalline cellulose pellets (Cellets 700) | | 73.980 | Non-pareille carrier pellet | Ph. Eur/NF |
| Hydroxypropyl cellulose (KLUCEL ® EF) | | 0.150 | Wet binder | Ph. Eur./NF |
| Talc | | 0.495 | Glidant | Ph. Eur./USP |
| Ethyl cellulose (N14) | | 3.750 | Functional coating | Ph. Eur./NF |
| Macrogol 6000 | | 0.938 | Plasticizer | Ph. Eur./USP |
| Ethanol (96%) | | 49.167* | Solvent | Ph. Eur. |
| Purified water | | 32.583* | Solvent | Ph. Eur./USP |
| HPMC capsule, size 3 | 46.000 | | Shell | Company Standard |
| Total | 126.063 | 80.063 | | |

*removed during processing (does not appear in the final product)

Example 4

One embodiment of the qualitative and quantitative composition of pramipexole extended release pellets according to the present invention (Formulation G) is shown in Table 4.

TABLE 4

Qualitative and Quantitative Composition of Pramipexole ER Capsule (Formulation G)

| Ingredient | mg per 0.75 mg capsule | mg per 0.75 mg capsule | Function | Reference to Standards |
|---|---|---|---|---|
| ER Pellets consisting of: | 82.088 | | | |
| Pramipexole dihydrochloride monohydrate | | 0.750 | Active ingredient | Corporate standard |
| Microcrystalline cellulose pellets (Cellets 700) | | 73.980 | Non-pareille carrier pellet | Ph. Eur/NF |
| Hydroxypropyl cellulose (KLUCEL ® EF) | | 0.150 | Wet binder | Ph. Eur./NF |
| Talc | | 0.645 | Glidant | Ph. Eur./USP |
| Ethyl cellulose (N14) | | 5.250 | Functional coating | Ph. Eur./NF |
| Macrogol 6000 | | 1.313 | Plasticizer | Ph. Eur./USP |
| Ethanol (96%) | | 68.333* | Solvent | Ph. Eur. |
| Purified water | | 33.667* | Solvent | Ph. Eur./USP |
| HPMC capsule, size 3 | 46.000 | | Shell | Company Standard |
| Total | 128.088 | 82.088 | | |

*removed during processing (does not appear in the final product)

Example 5

One embodiment of the qualitative and quantitative composition of pramipexole extended release pellets according to the present invention (Formulation H) is shown in Table 5.

TABLE 5

Qualitative and Quantitative Composition of Pramipexole ER Capsule (Formulation H)

| Ingredient | mg per 0.75 mg capsule | mg per 0.75 mg capsule | Function | Reference to Standards |
|---|---|---|---|---|
| ER Pellets consisting of: | 93.668 | | | |
| Pramipexole dihydrochloride monohydrate | | 0.750 | Active ingredient | Corporate standard |
| Microcrystalline cellulose pellets (Cellets 700) | | 73.980 | Non-pareille carrier pellet | Ph. Eur./NF |
| Hydroxypropyl cellulose (KLUCEL ® EF) | | 0.630 | Wet binder/ pore former | Ph. Eur./NF |
| Talc | | 1.995 | Glidant | Ph. Eur./USP |
| Methacrylic acid copolymer, Type B (EUDRAGIT ® S 100) | | 9.000 | Functional coating | Ph. Eur./NF |
| Ammonio methacrylate copolymer, Type B (EUDRAGIT ® RS 100) | | 4.500 | Functional coating | Ph. Eur./NF |
| Triethylcitrate | | 2.813 | Plasticizer | Ph. Eur./NF |
| Ethanol (96%) | | 250.200* | Solvent | Ph. Eur. |
| Purified water | | 30.000* | Solvent | Ph. Eur./USP |
| HPMC capsule, size 3 | 46.000 | | Shell | Company Standard |
| Total | 139.668 | 93.668 | | |

*removed during processing (does not appear in the final product)

Example 6

The batch formula for the two pramipexole extended release pellet formulations of Example 1 and 2 (Formulations D and E) is shown in Table 6. The batch size for the active ingredient layering is 1 kg, the batch size for the functional slow release film-coating of the active pellets is 530.748 g (Formulation D) and 549.600 g (Formulation E), corresponding to a theoretical batch size of 6000 capsules each.

TABLE 6

Composition Per Batch of Pramipexole ER Capsules (Formulation D and Formulation E)

| Ingredient | Grams per batch (formulation D) | Grams per batch (formulation E) |
|---|---|---|
| Active ingredient layering suspension: | | |
| Pramipexole dihydrochloride monohydrate | 10.000 | 10.000 |
| Hydroxypropyl cellulose | 2.000 | 2.000 |
| Talc | 1.600 | 1.600 |
| Purified water | 400.000* | 400.000* |
| | 13.600** | 13.600** |
| Active ingredient layering: | | |
| Active ingredient layering suspension | 13.600** | 13.600** |
| Microcrystalline cellulose pellets | 986.400 | 986.400 |
| Active pellets | 1000.000 | 1000.000 |
| ER coating suspension: | | |
| Methacrylic Acid Copolymer, Type B | 45.000 | 55.500 |
| Ammonio Methacrylate Copolymer, Type B | 22.500 | 27.750 |
| Triacetin | 10.998 | 13.602 |
| Talc | 2.250 | 2.748 |
| Ethanol (96%) | 1039.998* | 1285.002* |
| | 80.748** | 99.600** |

TABLE 6-continued

Composition Per Batch of Pramipexole ER Capsules (Formulation D and Formulation E)

| Ingredient | Grams per batch (formulation D) | Grams per batch (formulation E) |
|---|---|---|
| Functional film-coating: | | |
| Active pellets | 450.000 | 450.000 |
| ER coating suspension | 80.748** | 99.600** |
| Extended release pellets | 530.748 | 549.600 |
| Encapsulation: | | |
| Extended release pellets | 530.748 | 549.600 |
| Capsule shell | 276.000 | 276.000 |
| Total Weight | 806.748 | 825.600 |
| Number of capsules (actual depending on assay of pellets and yield) | 6000 | 6000 |

*removed during processing (does not appear in the final product)
**dry matter

Example 7

The batch formula for the two pramipexole capsule formulations of Example 3 and 4 (Formulations F and G) is shown in Table 7. The batch size for the active ingredient layering is 1 kg, the batch size for the functional slow release film-coating of the active pellets is 480.378 g (Formulation F) and 492.528 g (Formulation G), corresponding to a theoretical batch size of 6000 capsules each.

TABLE 7

Composition Per Batch of Pramipexole ER Capsules (Formulation F and Formulation G)

| Ingredient | Grams per batch (Formulation F) | Grams per batch (Formulation G) |
|---|---|---|
| Active ingredient layering suspension: | | |
| Pramipexole dihydrochloride monohydrate | 10.000 | 10.000 |
| Hydroxypropyl cellulose | 2.000 | 2.000 |
| Talc | 1.600 | 1.600 |
| Purified water | 400.000* | 400.000* |
|  | 13.600** | 13.600** |
| Active ingredient layering: | | |
| Active ingredient layering suspension | 13.600** | 13.600** |
| Microcrystalline cellulose pellets | 986.400 | 986.400 |
| Active pellets | 1000.000 | 1000.000 |
| ER coating suspension: | | |
| Ethyl cellulose (N14) | 22.500 | 31.500 |
| Macrogol 6000 | 5.628 | 7.878 |
| Talc | 2.250 | 3.150 |
| Purified water | 15.498* | 22.002* |
| Ethanol (96%) | 295.002* | 409.998* |
|  | 30.378** | 42.528** |
| Functional film-coating: | | |
| Active pellets | 450.000 | 450.000 |
| ER coating suspension | 30.378** | 42.528** |
| Slow release pellets | 480.378 | 492.528 |
| Encapsulation: | | |
| Slow release pellets | 480.378 | 492.528 |
| Capsule shell | 276.000 | 276.000 |
| Total Weight | 756.378 | 768.528 |
| Number of capsules (actual depending on assay of pellets and yield) | 6000 | 6000 |

*removed during processing (does not appear in the final product)
**dry matter

Example 8

The batch formula for the pramipexole pellet formulation of Example 5 (Formulation 1-1) is shown in Table 8. The batch size for the active ingredient layering is 1 kg, the batch size for the functional slow release film-coating of the active pellets is 562.008 g, corresponding to a theoretical batch size of 6000 capsules each.

TABLE 8

Composition Per Batch of Pramipexole ER Capsules (Formulation H)

| Ingredient | Grams per batch (Formulation H) |
| --- | --- |
| Active ingredient layering suspension: | |
| Pramipexole dihydrochloride monohydrate | 10.000 |
| Hydroxypropyl cellulose | 2.000 |
| Talc | 1.600 |
| Purified water | 400.000* |
| | 13.600** |
| Active ingredient layering: | |
| Active ingredient layering suspension | 13.600** |
| Microcrystalline cellulose pellets | 986.400 |
| Active pellets | 1000.000 |
| ER coating suspension: | |
| Methacrylic Acid Copolymer, Type B | 54.000 |
| Ammonio Methacrylate Copolymer, Type B | 27.000 |
| Hydroxypropyl cellulose | 2.880 |
| Triethyl citrate | 16.878 |
| Talc | 11.250 |
| Ethanol (96%) | 1501.200* |
| | 112.008** |
| Functional film-coating: | |
| Active pellets | 450.000 |
| ER coating suspension | 112.008** |
| Extended release pellets | 562.008 |
| Encapsulation: | |
| Slow release pellets | 562.008 |
| Capsule shell | 276.000 |
| Total Weight | 838.008 |
| Number of capsules (actual depending on assay of pellets and yield) | 6000 |

*removed during processing (does not appear in the final product)
**dry matter

Example 9

Pellets Prepared by Wet Extrusion

In order to achieve adequate content uniformity, 9 g of microcrystalline cellulose is mixed with 1 g of pramipexole. Then this mixture is mixed with 90 g of microcrystalline cellulose. The mixture is extruded in a twin screw extruder with an adequate amount of water (or binder solution), diameter of dye is 0.7 mm. The resulting extrudates are rounded in a spheronizer at 400 rpm. After drying pellets are sieved, the fraction of 0.8-1.1 mm is used for retardation as described in the previous examples. Table 9 provides some further examples of wet extrusion

TABLE 9

Further Examples for Wet Extrusion

| Example No. | Pramipexole (g) | Microcrystalline cellulose [g] | Binder [g] |
| --- | --- | --- | --- |
| 9 | 1 | 69 | 0 |
| 9a | 0.5 | 99.5 | 0 |
| 99b | 2 | 98 | 0 |
| 99c | 1 | 98 | 1 (povidone K25) |
| 99d | 1 | 98 | 1 (hydroxypropyl cellulose) |
| 99e | 0.5 | 98.5 | 1 (methyl cellulose) |

Example 10

Pellets Prepared by Melt Extrusion with Hydrophilic Excipients

In order to achieve adequate content uniformity, 9 g of polyethylene glycol 6000 (PEG) is mixed with 1 g of pramipexole. Then this mixture is mixed with 50 g of PEG 6000 and 40 g of poloxamer 188. The mixture is extruded in a twin screw extruder at 54° C., diameter of dye is 0.7 mm using a face cut granulator to achieve pieces of about 1 mm. These are rounded in a spheronizer at 400 rpm and 41° C. The pellets are sieved, the fraction of 0.8-1.1 mm is used for retardation as described in the previous examples. Table 10 provides some further examples of melt extrusion

TABLE 10

Examples for Melt Extrusion

| Example No. | Pramipexole [g] | PEG 6000 [g] | Poloxamer 188 [g] |
| --- | --- | --- | --- |
| 10 | 1 | 59 | 40 |
| 10a | 0.5 | 59.5 | 40 |
| 10b | 2 | 58 | 40 |
| 10c | 0.5 | 69 | 30 |

Example 11

Pellets Prepared by Melt Extrusion with Hydrophobic Excipients

In order to achieve adequate content uniformity, 9 g of stearyl alcohol is mixed with 1 g of pramipexole. Then this mixture is mixed with 90 g of stearyl alcohol. The mixture is extruded in a twin screw extruder at 51° C., diameter of dye is 0.7 mm using a face cut granulator to achieve pieces of about 1 mm. These are rounded in a spheronizer at 400 rpm and 41° C. The pellets are sieved, the fraction of 0.8-1.1 mm is used for retardation as described in the previous examples. Table 11 provides some further examples of melt extrusion.

TABLE 11

Further Examples for Melt Extrusion

| Example No. | Pramipexole [g] | Stearyl alcohol [g] | Cetyl alcohol [g] |
| --- | --- | --- | --- |
| 11 | 1 | 99 | 0 |
| 10a | 0.5 | 59.5 | 40 |
| 10b | 2 | 58 | 40 |
| 10c | 0.5 | 49 | 50 |

Example 12

Extended Release Pellets Prepared by Wet Extrusion

In order to achieve adequate content uniformity, 9 g of microcrystalline cellulose is mixed with 1 g of pramipexole. Then this mixture is mixed with 60 g of microcrystalline cellulose and 30 g of carbomer 97IP. The mixture is extruded in a twin screw extruder with an adequate amount of water (or binder solution), diameter of dye is 0.7 mm. The resulting extrudates are rounded in a spheronizer at 400 rpm. After drying, pellets are sieved, the fraction of 0.8-1.1 mm is filled into capsules. Table 12 provides some further examples of wet extrusion

TABLE 12

Further Examples for Extended Release Pellets Prepared by Wet Extrusion

| Example No. | Pramipexole [g] | Microcrystalline cellulose [g] | Extended release excipient [g] |
|---|---|---|---|
| 12 | 1 | 69 | 30 carbomer 971P |
| 12a | 0.5 | 69.5 | 30 carbomer 971P |
| 12b | 2 | 68 | 30 carbomer 971P |
| 12c | 1 | 69 | 30 EUDRAGIT ® S |
| 12d | 1 | 58 | 40 EUDRAGIT ® S |
| 12e | 1 | 44 | 30 EUDRAGIT ® S 25 carbomer 971P |

Example 13

Extended Release Pellets Prepared by Melt Extrusion

In order to achieve adequate content uniformity, 9 g of hydrogenated castor oil is mixed with 1 g of pramipexole. Then this mixture is mixed with 60 g of hydrogenated castor oil and 30 g of carnauba wax. The mixture is extruded in a twin screw extruder with an adequate amount of water (or binder solution), diameter of dye is 0.7 mm. The resulting extrudates are rounded in a spheronizer at 400 rpm. Pellets are sieved, the fraction of 0.8-1.1 mm is filled into capsules. Table 13 provides some further examples of melt extrusion

TABLE 13

Further Examples for Extended Release Pellets Prepared by Melt Extrusion

| Example No. | Pramipexole [g] | hydrogenated castor oil [g] | carnauba wax [g] |
|---|---|---|---|
| 13 | 1 | 69 | 30 |
| 13a | 0.5 | 69.5 | 30 |
| 13b | 2 | 68 | 30 |
| 13c | 1 | 59 | 40 |
| 13d | 1 | 78 | 21 |
| 12e | 1 | 83 | 16 |

Example 14

Extended Release Pellets Prepared by Hot Melt Granulation/Melt Pelletization In this process, agglomeration of active ingredient with excipients is promoted by the addition of low melting point, lipophilic binders, such as waxes, fats, fatty acids, fatty acid alcohols, and more water soluble polymers, such as poloxamers or polyethylene glycols. The binder is usually added to the other components as a powder. The binder is liquefied by heat generated either by friction during the mixing phase or by a heating jacket. Excipients suitable are, e.g., lactose, microcrystalline cellulose, and dibasic calcium phosphate. After melting and granulation of the mass, the resulting mass is either cooled down, screened and processed into tablets together with further excipients or, spheronized into pellets, which can be coated in addition, and filled into capsules

TABLE 14

Examples for Extended Release Pellets Prepared by Hot Melt Granulation/Melt Pelletization

| Example No. | Pramipexole [%] | Lactose | Stearyl alcohol [%] | carnauba wax [%] |
|---|---|---|---|---|
| 14 | 0.9 | 74.1 | 15 | 10 |
| 14a | 1.4 | 58.6 | 15 | 25 |
| 14b | 0.9 | 79.1 | 15 | 5 |

We claim:

1. An extended release pellet formulation comprising:
   an inert pellet core;
   a first layer being an active ingredient layer comprising pramipexole or a pharmaceutically acceptable salt thereof and one or more wet binders and at least one further excipient; and
   a second layer provided on the first layer, the second layer being an extended release coating comprising a mixture of 10 to 85% by weight of a pH-dependent enteric-coating polymer, which is an anionic polymer, and 15 to 75% by weight of a pH-independent water swelling polymer, which is a quaternary ammonium substituted acrylic polymer, and optionally additionally containing a pore-forming component,
   the resulting pellet having a close to zero order in vitro release characteristic at acidic pH values up to pH 6.8, an accelerated release above pH 6.8 and a more accelerated release above pH 7.3.

2. The extended release pellet formulation of claim 1, wherein the inert pellet core comprises a polysaccharide, cellulose, a cellulose derivative, a starch or a wax.

3. The extended release pellet formulation of claim 1, wherein the inert pellet core comprises saccharose and/or microcrystalline cellulose.

4. The extended release pellet formulation of claim 1, wherein the inert pellet core comprises microcrystalline cellulose.

5. The extended release pellet formulation according to claim 1, wherein the pH-dependent enteric-coating anionic polymer is a carboxylic acrylic polymer.

6. The extended release pellet formulation according to claim 5, wherein the carboxylic acrylic polymer is a partly methyl esterified methacrylic acid polymer, soluble above a pH value of 5.5.

7. The extended release pellet formulation according to claim 6, wherein the partly methyl esterified methacrylic acid polymer is soluble above a pH value of 7.0.

8. The extended release pellet formulation according to claim 1, wherein the quaternary ammonium substituted acrylic polymer has an ammonium substitution of about 5 to about 10 percent by weight.

9. The extended release pellet formulation according to claim 1, wherein the second layer contains a pore-forming component.

10. The extended release pellet formulation according to claim 9, wherein the amount of the pore-forming component is 1% to 25% by weight of the polymer mixture in the second layer.

11. The extended release pellet formulation according to claim 9, wherein the pore-forming component comprises at least one component selected from hydroxypropylcellulose, hydroxypropyl methylcellulose, polyvinylpyrrolidone and polyethylene glycol.

12. A capsule containing the extended release pellets of the formulation according to claim 1.

13. A capsule according to claim 12, wherein the amount of pramipexole or a pharmaceutically acceptable salt thereof contained in the extended release pellets in the capsule, is sufficient to provide a daily dose of pramipexole or a pharmaceutically acceptable salt thereof when administered at one time.

14. A method of manufacturing the extended release pellet formulation according to claim 1, comprising the steps of:
first, providing an inert starter pellet core;
second, applying a solution or dispersion of a first coating composition comprising pramipexole or a pharmaceutically acceptable salt thereof, at least a binder and optionally excipient(s) onto the inert starter pellet core to obtain an active ingredient pellet;
third, applying a solution or dispersion of a second coating composition comprising a mixture of the pH-dependent enteric-coating polymer and the pH-independent water swelling polymer, and optionally a pore-forming component as functional coating composition onto the active ingredient pellet obtained in the second step; and
optionally performing a manual screening after the second and/or third process step to remove agglomerates.

15. The method of manufacturing the extended release pellet formulation according to claim 14, wherein:
the second step of applying a solution or dispersion of a first coating composition is conducted by spraying the solution or dispersion of the coating composition onto the inert starter pellet core, wherein the pramexipole or a pharmaceutically acceptable salt thereof is used as unmilled material, dissolved/dispersed in a solvent together with the binder and optional excipient(s) and sprayed onto the inert starter pellet core and subsequently dried to obtain an active ingredient pellet; and
the third step of applying a solution or dispersion of a second coating composition is conducted by spraying the second coating composition solution/dispersion and a solvent onto the active ingredient pellet and subsequently drying the obtained extended release pellet.

16. A method for the treatment of Parkinson's disease and complications or disorders associated therewith which comprises administering to a patient the extended release pellet formulation according to claim 1.

* * * * *

UNITED STATES PATENT AND TRADEMARK OFFICE
CERTIFICATE OF CORRECTION

PATENT NO.        : 8,715,728 B2  
APPLICATION NO.   : 12/630271  
DATED             : May 6, 2014  
INVENTOR(S)       : Friedl et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 505 days.

Signed and Sealed this  
Eleventh Day of August, 2015

Michelle K. Lee  
*Director of the United States Patent and Trademark Office*